United States Patent
Stone et al.

(10) Patent No.: US 10,796,798 B1
(45) Date of Patent: Oct. 6, 2020

(54) SYSTEM AND METHOD OF A VIRTUAL SAND TRAY

(71) Applicants: Jessica Stone, Fruita, CO (US); Christopher Ewing, Fruita, CO (US)

(72) Inventors: Jessica Stone, Fruita, CO (US); Christopher Ewing, Fruita, CO (US)

(73) Assignee: Virtual Sandtray, LLC, Fruita, CO (US)

( * ) Notice: Subject to any disclaimer, the term of this patent is extended or adjusted under 35 U.S.C. 154(b) by 0 days.

(21) Appl. No.: 15/088,514

(22) Filed: Apr. 1, 2016

(51) Int. Cl.
*G16H 50/20* (2018.01)
*G16H 15/00* (2018.01)
*A61B 5/16* (2006.01)

(52) U.S. Cl.
CPC ............. *G16H 50/20* (2018.01); *A61B 5/165* (2013.01); *G16H 15/00* (2018.01)

(58) Field of Classification Search
CPC .......... G06F 17/30017; G06F 19/3418; G06F 19/345; G06Q 50/22; A61B 5/165
See application file for complete search history.

(56) References Cited

U.S. PATENT DOCUMENTS

| 9,104,791 | B2 * | 8/2015 | Cohen | G06F 19/321 |
| 2005/0244798 | A1 * | 11/2005 | Zernzach | G09B 23/28 434/236 |
| 2007/0166690 | A1 * | 7/2007 | Johnson | G09B 5/14 434/365 |
| 2008/0222555 | A1 * | 9/2008 | Coyne | G06T 13/00 715/781 |
| 2012/0320145 | A1 * | 12/2012 | Kahn | G06F 19/3418 348/14.08 |
| 2013/0149683 | A1 * | 6/2013 | Steerman | G09B 19/00 434/236 |
| 2015/0310643 | A1 * | 10/2015 | Rzeszotarski | G06T 13/20 345/440 |

* cited by examiner

*Primary Examiner* — Jason Skaarup
(74) *Attorney, Agent, or Firm* — Spencer Fane LLP; Steven J. Laureanti

(57) ABSTRACT

A system and method are disclosed for generating a report for an internal state of a patient. The system includes a computer configured to generate a virtual environment comprising a base layer and provide one or more object models to be placed in the virtual environment. The computer is further configured to provide one or more tools to manipulate the virtual environment and the one or more object models and automatically determine an internal state of a patient based, at least in part, on the selection and manipulation of the one or more object models and the manipulation of the virtual environment.

18 Claims, 21 Drawing Sheets

SYSTEM AND METHOD OF A VIRTUAL SAND TRAY

TECHNICAL FIELD

The disclosure relates generally to a system and method for generating a virtual environment and more particularly to therapy analysis using a virtual sand tray.

BACKGROUND

Traditional psychotherapy seeks to help individual health and well-being by improving or overcoming unhelpful behaviors, beliefs, thoughts, and emotions. One tool employed by some specialists utilizes observing a patient placing objects in a sandbox to understand the internal state of a patient. For these traditional sand trays, a patient is allowed to create an environment by placing miniature objects, such as trees, buildings, animals, and people in the sand tray. By observing the placement and selection of the objects, the specialist may gain insight into the subconscious representative of what is going on internally with the patient. However, sand trays have many disadvantages. For example, a large amount of space is required to store the sand tray and the large number of objects to be placed in the tray (often, a room filled with shelves). Another disadvantage is the limited amount of configurations of the objects, based on physical constraints. Still another disadvantage is that a patient is required to travel to the location of the sand tray, which is inconvenient. In addition, because there is limited space for sand trays, the sand tray of an individual patient may not be preserved between therapy sessions, and each use would require the patient to rebuild the sand tray from the beginning. These disadvantages are undesirable.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

DETAILED DESCRIPTION

Figure 1:
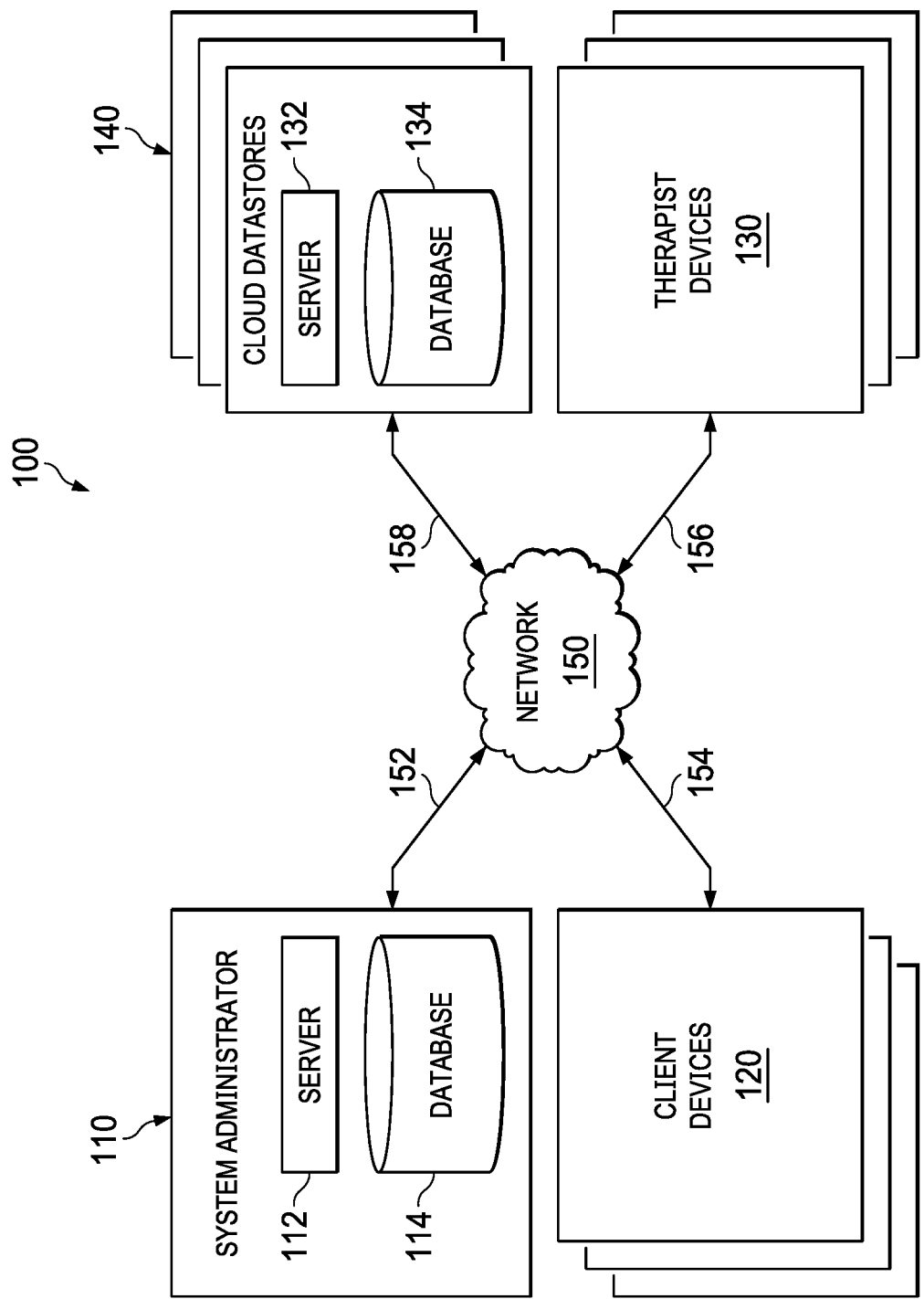
FIG. 1 illustrates an exemplary system according to a first embodiment.

Aspects and applications of the invention presented herein are described below in the drawings and detailed description of the invention. Unless specifically noted, it is intended that the words and phrases herein be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that embodiments of the present invention may be practiced without these specific details. In other instances, known structures and devices are shown and/or discussed more generally in order to avoid obscuring the invention. In many cases, a description of the operation is sufficient to enable one of ordinary skill in the applicable art to implement the various forms of the invention. It should be appreciated that there are many different and alternative configurations, devices and technologies to which the disclosed inventions may be applied. The full scope of the present disclosure is not limited to the examples described below.

The following disclosure relates to one or more aspects of a virtual sand tray. According to a first aspect, the virtual sand tray may provide a virtual environment and object models that can be manipulated by a user. According to some embodiments, modifications to the environment and placement and modifications to the object models may be recorded, and the recordings transmitted to a specialist, who may gain insight into the internal state of the user.

According to a further aspect, the virtual sand tray system provides an interface for the administration of multiple users of the virtual sand tray and the secured sharing of the virtual environments created by the users. Such sharing may be between various users, including transmitting the virtual environment and/or a recording of the creation of the virtual environment to a specialist or supervisor for interpretation.

FIG. 1 illustrates an exemplary system 100 according to a first embodiment. System 100 comprises a system administrator 110, one or more secondary devices 120, one or more primary devices 130, one or more cloud datastores 140, a network 150, and communication links 152, 154, 156, and 158. Although a single system administrator 110, one or more secondary devices 120, one or more primary devices 130, one or more cloud datastores 140, and a single network 150, are shown and described; embodiments contemplate any number of system administrators 110, any number of secondary devices 120, any number of primary devices 130, any number of cloud datastores 140, or any number of networks 150, according to particular needs.

System 100 may operate on one or more computers that are integral to or separate from the hardware and/or software that support system administrator 110, one or more secondary devices 120, one or more primary devices 130, and one or more cloud datastores 140. Computers may include any suitable input device, such as a keypad, mouse, touch screen, microphone, or other device to input information. An output device may convey information associated with the operation of system 100, including digital or analog data, visual information, or audio information. Computers may include fixed or removable computer-readable storage media, including a non-transitory computer-readable medium, magnetic computer disks, flash drives, CD-ROM, in-memory device or other suitable media to receive output from and provide input to system 100. Computers may include one or more processors and associated memory to execute instructions and manipulate information according to the operation of system.

System administrator 110, one or more secondary devices 120, one or more primary devices 130, and one or more cloud datastores 140 may each operate on separate computers or may operate on one or more shared computers. Each of the one or more computers may be a work station, personal computer (PC), network computer, notebook computer, tablet (such as an APPLE® IPAD® tablet computer), personal digital assistant (PDA), cell phone, telephone, wireless data port, or any other suitable computing device.

In an embodiment, one or more users, such as an administrator, specialist, therapist, patient, client, or other users may be associated with system 100. For example, one or more administrators may be associated with system administrator 110. These one or more administrators may handle, for example, administration of virtual sand tray system and/or one or more related tasks within system 100. In addition, or as an alternative, these one or more administrators associated with system administrator 110 may include, for example, one or more computers programmed to autonomously handle, among other things, system administration and/or one or more related tasks within system 100.

In one embodiment, one or more secondary devices 120 represent one or more devices associated with a client. A client may be any user of virtual environment 300, such as a patient, video game player, or any other user. Secondary device 120 permits portability by its decreased space requirements compared to a traditional sand tray, which allows use of a virtual environment 300 (FIG. 3) in virtually any treatment setting, such as the home, therapist office, hospital, or any other location because it eliminates the need for the large space requirement to store non-virtual sand trays and associated objects.

According to some embodiments, secondary device 120 may run virtual environment 300 directly on the secondary device 120, or it may host an interface to securely access a remotely run program hosted on, for example, system administrator 110, primary device 130, or cloud datastore 140. Similarly, secondary device 120 may store data directly on the secondary device 120, or remotely on system administrator 110, primary device 130, or cloud datastores 140, according to particular needs.

In an embodiment, one or more primary devices 130 represent one or more devices associated with a particular therapy practice, clinic, hospital, specialist, therapist, or the like. One or more primary devices 130 may be associated with one or more users such as a specialist (including, for example, a therapist, therapy assistant, or therapy supervisor), who may handle interpretation of virtual environment 300 (FIG. 3), interpretation of therapy reports, or one or more related tasks within system 100. In addition, or as an alternative, these one or more specialists, associated with primary devices 130 may include, for example, one or more computers programmed to autonomously handle, among other things, interpretation of virtual environment 300, interpretation of therapy reports, and/or one or more related tasks within system 100.

For example, when a client uses a secondary device 120 to interact with virtual environment 300 (see FIG. 3), one or more reports or recordings may be generated that illustrate the internal state of a client. A specialist may receive and view the reports or recordings on the primary device 130 to understand or diagnose the client. Primary devices 130 may also collect this, and other information, for use in scientific research. Additionally, primary devices 130 may provide options and settings for controlling virtual environment 300 that is displayed on the secondary devices 120. Such options and settings may be used to present particular object models 306, manipulations of object models 306, and/or manipulations of virtual environment 300 to a client in a directed manner to help guide the client in a therapeutic fashion, such as, for example, confronting particular fears or dealing with particular emotional triggering events.

Although system administrator 110, secondary devices 120, and primary devices 130 are described as being associated with particular users or with particular tasks, embodiments contemplate system administrator 110, secondary devices 120, and primary devices 130 may be used for any task or by any user according to particular needs, as described herein. For example, although system administrator 110, secondary devices 120, and primary devices 130 are described as separate devices, embodiments contemplate that a single device may perform the operations of any or all of the devices, but where the separate operations are restricted based on a username and password. For instance, a single tablet computer may serve as a secondary device 120 when a client logs into the device, but the same tablet computer may serve as a primary device 130 when a specialist logs into the device. Similarly, some tasks associated with a particular user may be performed by other users. For example, a single user may act as both an administrator and as a specialist, depending on the particular role of the user in relation to system 100.

Cloud datastores 140 comprise server 132 and database 134. Cloud datastores 140 provide for the secure storage of data and hosting of programs or applications for system administrator 110, secondary devices 120, and primary devices 130. According to embodiments, server 132 of cloud datastores 140 may host and run one or more runtime processes associated with virtual environment 300. Database 134 may store any data of system 100, including model data 232, recorded data 234, and reports 236 (see FIG. 2) for secure storage and retrieval, and may include one or more processes for deleting confidential data after a particular event, time period, or both, as described in more detail blow.

In one embodiment, system administrator 110 is coupled with network 150 using communications link 152, which may be any wireline, wireless, or other link suitable to support data communications between system administrator 110 and network 150 during operation of system 100. One or more secondary devices 120 are coupled with network 150 using communications link 154, which may be any wireline, wireless, or other link suitable to support data communications between one or more secondary devices 120 and network 150 during operation of system 100. Primary devices 130 are coupled with network 150 using communications link 156, which may be any wireline, wireless, or other link suitable to support data communications between computers 130 and network 150 during operation of system 100. Cloud datastores 140 are coupled with network 150 using communications link 158, which may be any wireline, wireless, or other link suitable to support data communications between cloud datastores 140 and network 150 during operation of system 100.

Although communication links 152, 154, 156, and 158 are shown as generally coupling system administrator 110, one or more secondary devices 120, one or more primary devices 130, and cloud datastores 140 with network 150, system administrator 110, one or more secondary devices 120, one or more primary devices 130, and cloud datastores 140 may communicate directly with system administrator 110, one or more secondary devices 120, one or more primary devices 130, and cloud datastores 140, according to particular needs.

In another embodiment, network 150 includes the Internet and any appropriate computer or communication network, such as, for example, local area networks (LANs), metropolitan area networks (MANs), or wide area networks (WANs) coupling system administrator 110, one or more secondary devices 120, one or more primary devices 130, and cloud datastores 140. For example, data may be maintained by system administrator 110, secondary devices 120, primary devices 130, and cloud datastores 140 at one or more locations external to system administrator 110, secondary devices 120, primary devices 130, and cloud datastores 140 and made available to one or more users of system 100 using network 150 or in any other appropriate manner. Those skilled in the art will recognize that the complete structure and operation of network 150 and other components within system 100 are not depicted or described. Embodiments may be employed in conjunction with known communications networks and other components.

To further explain the operation of system 100, an example is now given. In the following example, system administrator 110 generates and provides a virtual environment accessible to one or more secondary devices 120 and primary devices 130. The virtual environment provides a platform, which may be graphically represented as a sand tray that a user may manipulate by, for example, virtually digging into or building up a base layer using a tool, such as a shovel. Further, the virtual sandbox 110 provides a collection of object models (such as, for example, animals, buildings, characters, dinosaurs, fantasy creatures, food, furniture, holiday-themed models, insects, letters, military equipment, monsters, people, plants, props, science-fiction-themed models, ships, treasure, weapons, and other such models). Virtual sandbox 110 provides a user interface that permits a user to add such object models to the base layer, and manipulate the models by, for example, size, placement, color, clothing, animation, facial expression, hair style, mood, and other manipulations. In one embodiment, a user creates a virtual environment and the secondary device 120 records the sequence and timing of the creation and manipulations of the virtual environment. This may include, for example, recording the order of the placement of models, the amount of time choosing a model, the selection between a positive-oriented model and a negative-oriented model, and other like decisions and manipulations as described in more detail below. In addition, or as an alternative, secondary device 120 records a video or picture of the creation of the environment or a beginning, intermediate, or final state of the environment that may be stored locally or remotely and transmitted securely to an administrator or specialist, according to particular needs. Based on the recorded data of virtual environment 300, a primary device 130 and/or an associated specialist may determine an internal state of the client using secondary device 120.

Figure 2:
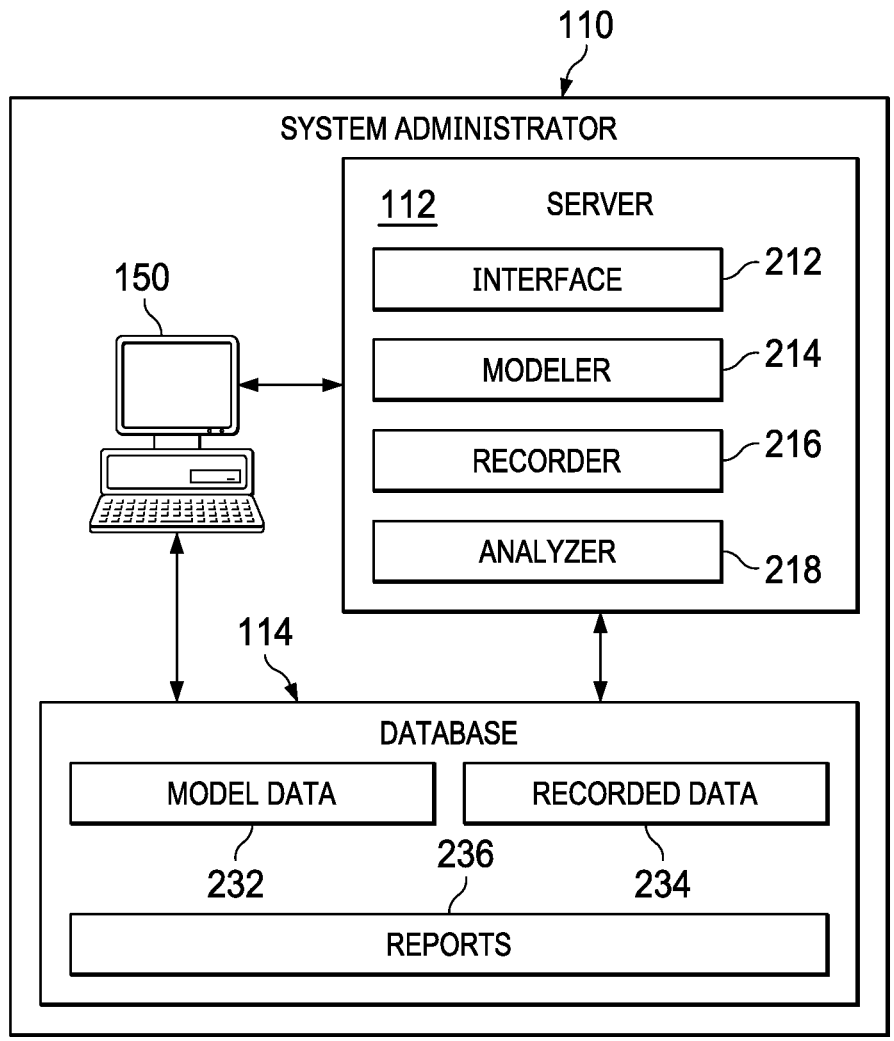
FIG. 2 illustrates the virtual sand tray of FIG. 1 in greater detail in accordance with an embodiment.

FIG. 2 illustrates system administrator 110 of FIG. 1 in greater detail, in accordance with an embodiment. As discussed above, system administrator 110 comprises one or more computers at one or more locations including associated input devices, output devices, non-transitory computer-readable storage media, processors, memory, or other components for receiving, processing, storing, and communicating information according to the operation of system 100. As discussed in more detail below, system administrator 110 comprises server 112 and database 114. Although system administrator 110 is shown as comprising server 112 and database 114; embodiments contemplate any suitable number of computers, servers, or databases internal to or externally coupled with system administrator 110. In addition, or as an alternative, system administrator 110 may be located internal or external to one or more secondary devices 120, primary devices 130, or cloud datastores 140.

Server 112 of system administrator 110 comprises an interface 212, modeler 214, recorder 216, and analyzer 218. Although a particular configuration of server 112 is shown and described, embodiments contemplate any suitable number or combination of interfaces, modelers, recorders, or analyzers located at one or more locations, local to, or remote from, system administrator 110, according to particular needs. Furthermore, interface 212, modeler 214, recorder 216, and analyzer 218 may be located at one or more locations, local to, or remote from, system administrator 110 such as on multiple servers or computers at any location in system 100.

Interface 212 of server 112 may provide one or more software or hardware interfaces that control the administration and operation of system administrator 110. For example, interface 212 may comprise a touchscreen menu system that permits the registration of users, classifying users as administrators, specialists, or clients, managing user accounts, saving, loading, and sharing virtual environments, which may also be referred to as "trays," changing language settings, and one or more related tasks in the system.

For example, according to some embodiments, interface 212 provides saving, loading, and sharing trays. When saving a tray, interface 212 may record the state of the modeler 214 (and any models represented therein) such that the virtual environment represented by the modeler 214 may be recreated when the state is loaded. Additionally, interface 212 may permit the sharing of any saved states of the virtual environment with other users of the system administrator 110, secondary devices 120, or primary devices 130.

According to some embodiments, interface 212 may classify users according to various classes, such that only certain users, such as specialists, are permitted to share saved states. Due to the confidential nature of psychological evaluations, these saved states may be highly sensitive. Therefore, interface 212 may provide for encrypting or data protection of saved states.

According to some embodiments, interface 212 comprises one or more tools to interface with modeler 214 and manipulate the virtual environment or object models.

Figure 3:
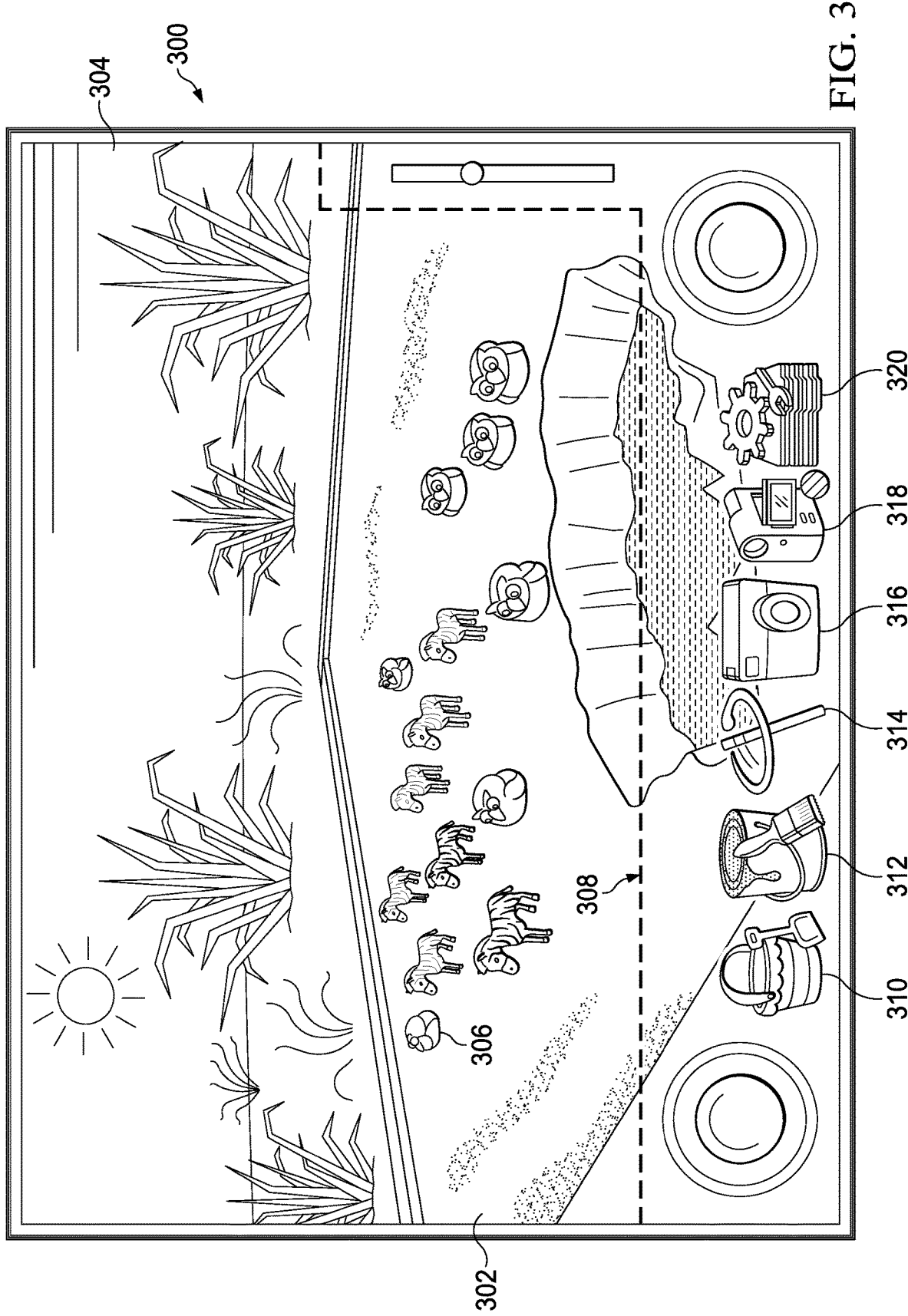
FIG. 3 illustrates an exemplary virtual environment according to a particular embodiment.

FIG. 3 illustrates an exemplary virtual environment 300 according to a particular embodiment. Virtual environment 300 may comprise base layer 302, skybox 304, object models 306, and control interface 308. As will be described in more detail below, interface 212 provides one or more tools of control interface 308 that permit a user to, for example, alter the topography of base layer 302 using shovel 310, color or change the texture of a surface using paint brush 312, add object models 306 to virtual environment 300 using wand 314, take a snapshot of the virtual environment using camera 314, record a video of the virtual environment using video camera 316, and alter the background in skybox 304 using settings icon 320.

Modeler 214 of server 112 may generate a virtual environment 300 based on one or more underlying models based, at least in part, on model data 232 of database 220. Modeler 214 may receive model data 232 and display a virtual environment 300 comprising, for example, a graphical representation of a three-dimensional virtual environment 300, which may comprise base layer 302, representing the ground, a skybox 304, representing the distant background and/or sky, and any number of object models 306 that correspond to any real-world person, character, item, tool, or any other physical thing. According to embodiments, modeler 214 comprises a graphical engine that uses the underlying model data 232 to generate a virtual environment 300, and generate manipulations from one or more tools of control interface 308 to manipulate that virtual environment 300. For example, modeler 214 may interface with the one or more tools, such as, for example, modeling the change in topography from digging or building with shovel 310, altering the texture of surfaces by paint brush 312, and/or using wand 314 to alter the placement, arrangement, sizing, and removal of one or more object models 306, as described in more detail below.

According to some embodiments, modeler 214 comprises a graphical engine that generates a signal suitable for display on a three-dimensional virtual reality display. The virtual reality signal may be displayed on any suitable virtual reality display device, such as a headset, three-dimensional display-capable monitor, or any other suitable display device for perceiving three-dimensional images.

Recorder 216 of server 112 may record one or more manipulations or states of virtual environment 300 and store the result as recorded data 234. For example, recorder 216 may comprise a visual recording of the graphical representation of virtual environment 300, either by a still image or a video. Images and video may also be accompanied by recorded sounds, such as narration by a client describing his or her actions or thoughts while building or manipulating virtual environment 300. According to some embodiments, recorder 216 also provides an interface to view the recorded image or video. In addition, or as an alternative, recorder 216 may record data corresponding to the placement and manipulations of the object models 306 in virtual environment 300 that may be useful to interpret a user's interaction with virtual environment 300. In one embodiment, recorder 216 stores coordinates of object model 306 placements within virtual environment 300, the physical or temporal relationship between various object models 306, the order that various object models 306 were chosen, the time needed to select an object model 306, moods or emotional states associated with one or more object models 306, or various other data points associated with virtual environment 300.

Analyzer 218 of server 112 may receive recording data 234 from recorder 216 and generate an analysis or report of the data, stored as reports 236. Such analysis or report may comprise a summary, chart, graph, or other representation of data that describes recorded data 234. Analyzer 218 may sort, categorize, or compute variables or parameters based on recorded data 234 to generate insights into a client's mental state. For example, analyzer 218 may generate a report 236 comprising a summary of chosen object models 306 (including, for example, an emotional state chosen or associated one or more of the models), constructive or destructive behaviors in the virtual world, or selection of one or more negative or positive environmental selections. By way of example only, such a summary may include that a client chose a character model to place in the environment and then chose to change the facial expression of the character to represent sadness. In addition, or as an alternative, a summary may indicate that a user chose to change a water feature to poison or lava. Other data or information may be included according to particular needs.

Database 114 of system administrator 110 comprises model data 232, recorded data 234, and reports 236. Although, database 114 is shown and described as comprising model data 232, recorded data 234, and reports 236; embodiments contemplate any suitable number or combination of these, located at one or more locations, local to, or remote from, system administrator 110, according to particular needs.

Model data 232 may comprise any information or data necessary to represent object models 306 and virtual environment 300. Such model data 232 may include wireframe models, coordinates, textures, any type of mapping data (including texture mapping, and the like), animations, behaviors (including emotions and expressions), interactions between models, and other like information and data. Model data 232 may be used by modeler 214 to generate the virtual environment, by recorder 216 to record and/or reproduce the virtual environment, and by analyzer 218 to correlate the manipulation of the virtual environment to reports 236.

Recorded data 234 may comprise any graphic, video, audio, or any media that corresponds to a created virtual environment and any accompanying sounds or narration. In addition, or as an alternative, recorded data 234 may comprise a recording of the underlying model data 232 that allows any manipulation or state of virtual environment 300 to be stored, transmitted, or received, as discussed below.

Reports 236 may comprise any categorization, sorting, or calculation based on recorded data 234 that permits interpretation of any manipulations or states of the virtual environment. Such reports 236 may provide insight into the internal state of a user of secondary device 120. According to some embodiments, recorded data 234 and/or reports 236 are transmitted or shared securely between one or more users of system 100.

Additionally, or in the alternative, recorded data 234 and reports 236 may be stored securely on cloud datastores 140 or locally on secondary devices 120 and primary devices 130. Because the information stored within recorded data 234 and reports 236 is highly sensitive, some specialists or clients may wish that the data does not leave the secondary device 120 or primary device 130 on which it is generated. However, as discussed below, embodiments contemplate the secure sharing of recorded data 234 and reports 236 by cloud datastore 140, where any data shared by secondary devices 120 or primary devices 130 is automatically deleted after a limited amount of time, automatically deleted after it is accessed, or automatically deleted within a certain time period after it is accessed.

Figure 4:
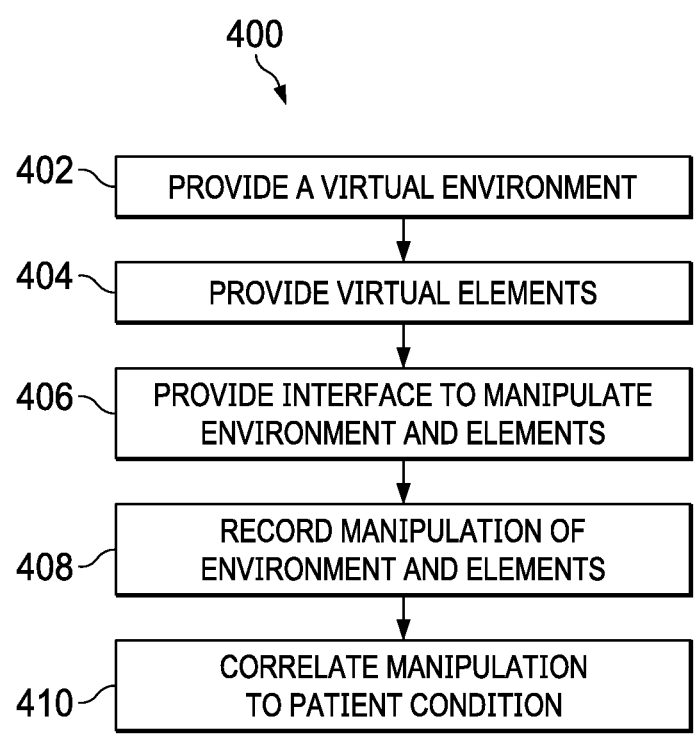
FIG. 4 illustrates a method of generating a report from the virtual environment according to an embodiment.

FIG. 4 illustrates a method 400 of generating a report 236 from a virtual environment 300 according to an embodiment. The process of the method 400 proceeds by one or more activities, which although described in a particular order may be performed in one or more permutations, according to particular needs. Method 400 begins at activity 402 where modeler 212 generates a virtual environment 300 based, at least in part, on model data 232. This virtual environment 300 may initially comprise a "blank slate" for a user to begin manipulating by altering textures, topography, or model placement. In addition, or as an alternative, this initial virtual environment 300 may comprise a preloaded scenario, such as a previously saved state by that client or a particular environment chosen by a specialist to guide the client in a directed fashion.

At activity 404, interface 212 provides a selection object models 306 and may be chosen by a user to place in virtual environment 300. Object models 306 may comprise any suitable character, animal, fantasy creature, building, or any other like object capable of being represented graphically, as described above.

At activity 406, interface 212 of system administrator 110 provides for the selection and manipulation of virtual environment 300, one or more object models 306, and/or one or more virtual elements by one or more settings or tools of tool interface 308. Tools may comprise objects useful for manipulating virtual environment 300 and models 306, as will be described in more detail below.

At activity 408, recorder 216 of system administrator 110 records the selection and manipulation of virtual environment 300 and object models 306. For example, recorder 216 may store in recorded data 234 a video of virtual environment 300 along with a narration recorded by the client describing the client's manipulation of virtual environment 300 and object models 306.

At activity 410, analyzer 218 correlates recorded data 234 of activity 408 to one or more internal states. Analyzer 218 may automatically correlate recorded data 234 to one or more internal states by, for example, pattern recognition of recorded data 234 (such as a screenshot, video, or saved state) or by generating a report 236 for interpretation by primary devices 130. In addition, or as an alternative, embodiments contemplate a user-directed interaction with virtual environment 300. For example, a client may interact with virtual environment 300 as a video game. System administrator 110 may generate a report analyzing the internal state of the user by monitoring how the user interacts with virtual environment 300 in an automatic and non-directed manner. According to some embodiments, virtual environment 300 may present one or more tasks to the user, and generate a report analyzing the internal state of the user based on what object models 306 or manipulations to virtual environment 300 are used in completing the task. For example, primary device 130 may generate a state of a virtual environment 300 specific to an internal state of a user. The state of virtual environment 300 may be transmitted from the primary device 130 to secondary device 120. As the client interacts with the state of virtual environment 300 generated by primary device 130, information about the internal state of the client is analyzed and a report is generated for primary device 130.

In addition, although FIG. 4 illustrates one embodiment of an exemplary method 400, various changes may be made to method 400 without departing from the scope of embodiments described herein. In addition, the following FIGURES illustrate various features and aspects of the above-described system and method in greater detail.

Figure 5:
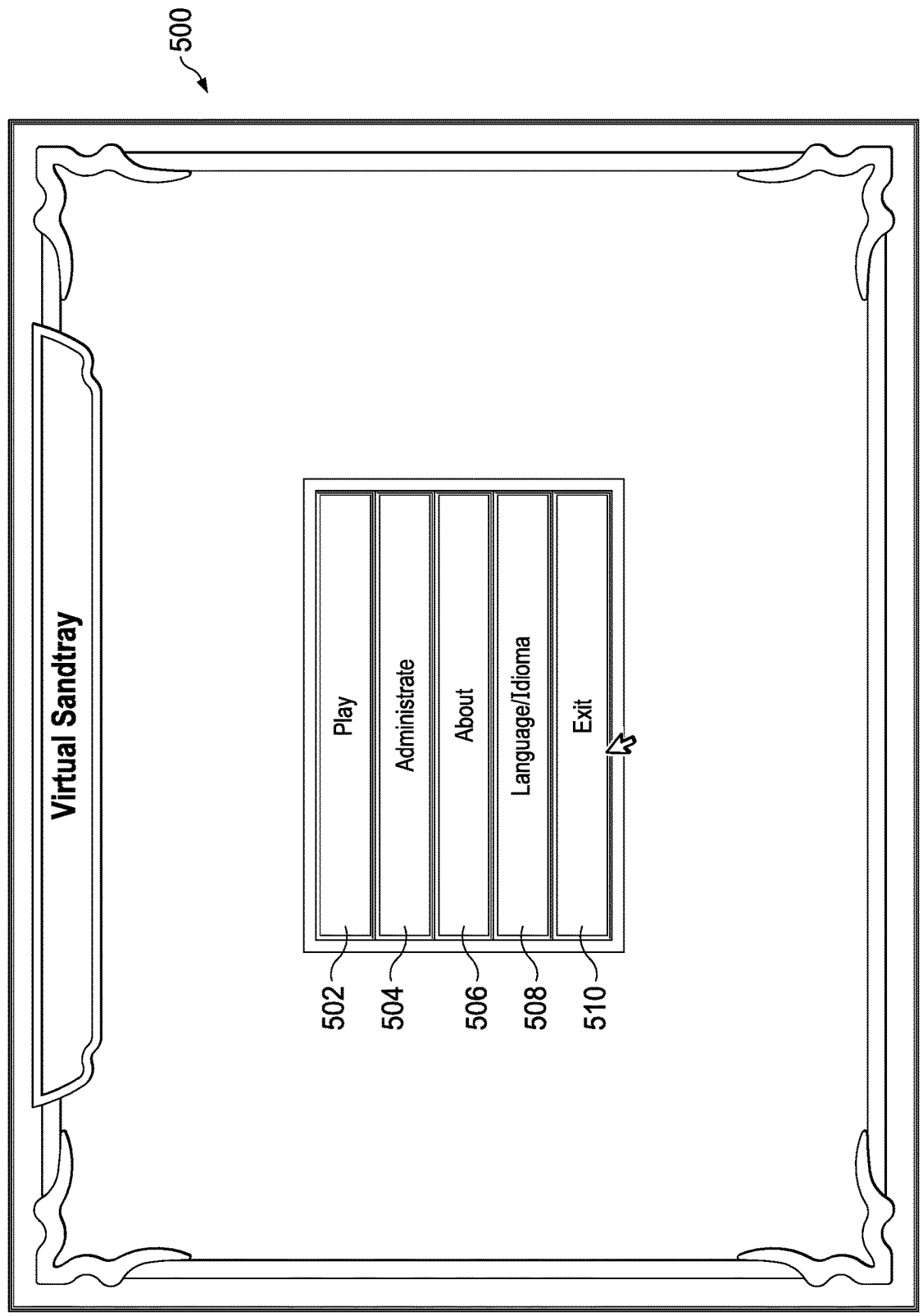
FIG. 5 illustrates an exemplary main menu after an administrator logs into the system.
Figure 6:
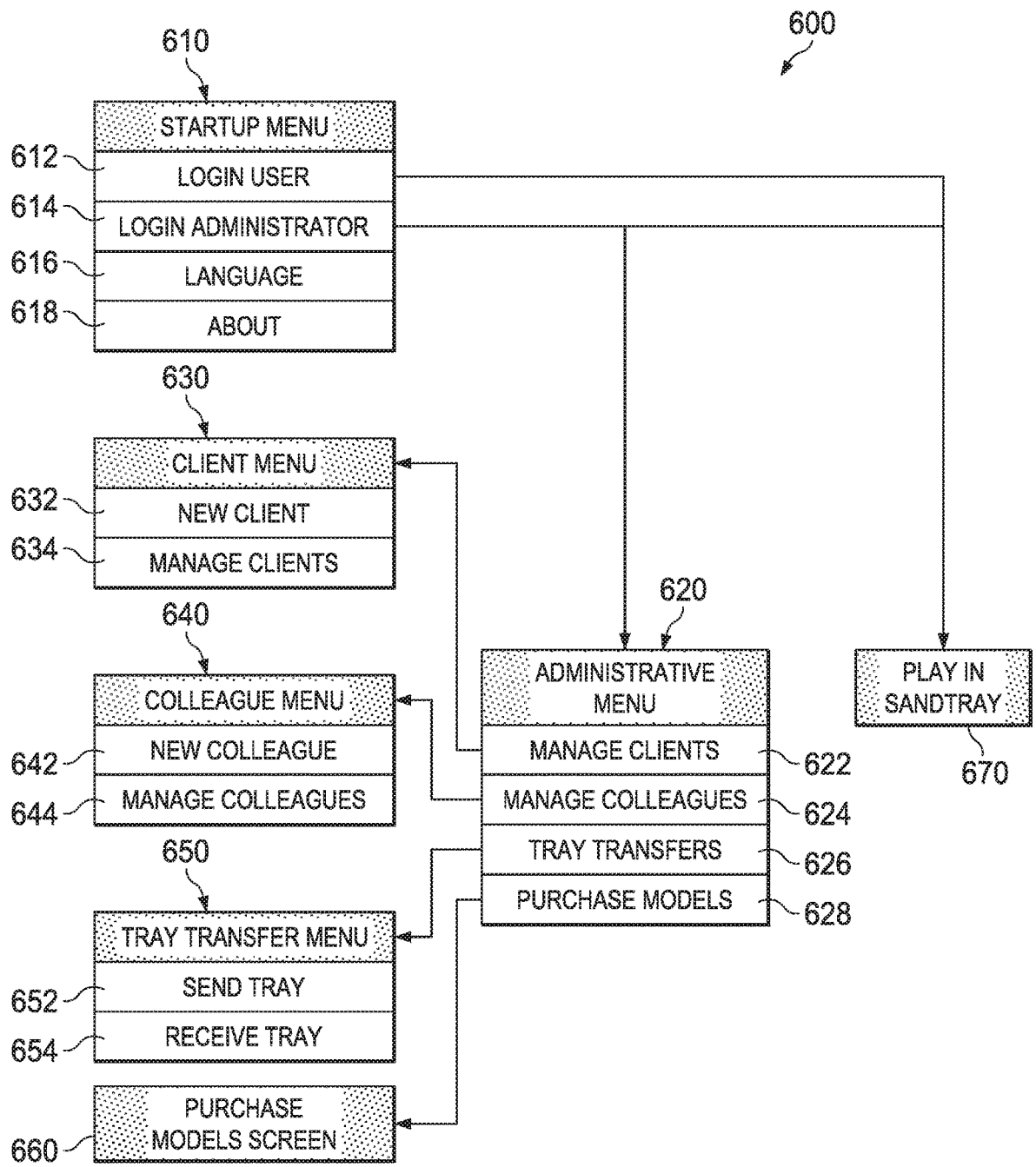
FIG. 6 illustrates an exemplary hierarchical menu structure for administration and configuration of the main menu according to an embodiment.

FIG. 5 illustrates an exemplary main menu 500 after an administrator logs into system 100. Each button 502-510 may initiate an action in system 100 directly. For example, selection of play button 502 in interface 212 may cause modeler 214 to generate a virtual environment according to activity 302 above. In addition, or as an alternative, each button 502-510 on main menu 500 may correspond to a menu or menu option of a menu structure 600, as shown in FIG. 6. For example, the button for administrate 504 may correspond to a first layer of a hierarchical menu system 600 for altering settings relating to administration of the system 100.

FIG. 6 illustrates an exemplary hierarchical menu structure 600 for administration and configuration of main menu 500 according to an embodiment. Although a particular arrangement of various levels of the menu are illustrated, embodiments contemplate any suitable combination or arrangement of menu options, according to particular needs.

Prior to main menu 500 of FIG. 5, and when virtual environment 300 is initiated, interface 212 may present startup menu 610. Startup menu 610 may comprise options, such as, for example: user login 612, administrator login 614, language 616, and about 618. User login 612 may comprise entering in a username and password or otherwise choosing and validating a user account that will be associated with a session of virtual environment 300. Similarly, administrator login 614 may comprise choosing and validating a user account with administrator access. Such administrator access may allow greater control (such as additional menu options) for a user with administrator privileges, such as an administrator. For example, system administrator 110 may prevent a client from accessing saved states or trays of other clients and prevent the client access to purchase additional models or options. Selection of exit button 510 may log a user or administrator out of virtual environment 300.

Language 616 of hierarchy 600 is accessed by language button 508 of main menu 500 of FIG. 5 and provides for changing the language of menus in options to any suitable language. About 618 of hierarchy 600 is accessed by about button 506 of main menu 500 of FIG. 5 and presents information about virtual environment 300.

After administrator login and selection of administrate button 504, as described above, administrative menu 620 is launched. Administrative menu 620 comprises options that are permitted to be used only by administrators, such as, for example, manage clients 622, manage colleagues 624, tray transfers 626, and/or purchase models 628.

Selection of the menu option for manage clients 622 generates client menu 630, which comprises two menu options: new client 632 and manage clients 634. New client 632 permits administrator to add one or more new clients by, for example, storing a username and password associated with a user account. Manage clients 634 permits an administrator to add, delete, or otherwise change data associated with user accounts.

Selection of the menu option for manage colleagues 624 generates colleague menu 640. Colleagues may represent one or more shared connections with secondary devices 120 of other users, such as clients or administrators, with which a current secondary device 120 shares recordings, reports, trays, or states. Manage colleagues 624 menu option permits adding a new colleague 642 or managing colleagues 644 to add, delete, or otherwise change data associated with colleagues.

Selection of the menu option for tray transfers 626 from administrative menu 620 generates tray transfer menu 650, which comprises two options: send tray 652 and receive tray 654. Send tray 652 comprises an option to share a report, tray, recording, state, or other data between a secondary device 120 and a primary device 130. For example, trays may be shared between a secondary device 120 and a primary device 130, or between a primary device 130 associated with a specialist and another primary device 130 associated with a supervisor of the specialist. Trays may also be shared to help in consultation, discussing cases with colleagues, or other like situations.

Send tray 652 may only permit the sharing of trays with colleagues that have been added by new colleague 642 menu option, this association may be termed a "friendship." To create a friendship, so that users can share files, a user may be required to enter the recipient's email. The recipient may then get an email stating that the user associated with sending the friendship request would like to become a friend. When a user associated with the recipient of the friendship request, clicks on a link in the email to confirm the friendship, virtual tray system 100 permits sending and receiving trays between those two users. System administrator 110 also permits deleting the friendship by either user.

Send tray 652 may additionally require that a user login as an administrator. Upon successful login, a user may select send tray 652 and a window may open up, where a user may select one or more users with a friendship to that user account. An option may be presented to select one or more trays, which may be then sent by a send tray button. Additionally, each user may receive a notification when the tray has been sent and/or received. According to some embodiments, a shared tray is stored on one or more of system administrator 110, secondary device 120, primary device 130, or any one or more databases (such as a cloud database 140) coupled to system 100. A shared tray may also be purged from a database or device within a limited time period, such as seven days, after the tray is sent.

Receiving a tray may be initiated by receive tray 654 menu option, as illustrated on hierarchy 600. Upon login as an administrator, a user may select receive tray 654 and a window may open up, where a user may select one or more friends or trays with which the user has been sent a tray. Upon selection of the tray or in response to selecting a download button, the tray may be securely downloaded to primary device 130. According to some embodiments, the trays are secured by storing the tray in a proprietary format that is not readable by other programs (such as a text reader), and the file may be additionally encrypted as well. Additionally, the limitation of sharing trays only with other friends, that must be confirmed by both users and which may be terminated at any time, enhances security as well.

Returning to hierarchy 600, selection of purchase models 628 from the administrative menu 620 provides options for purchasing additional packages of object models 306, such as objects associated with a particular theme or category. According to some embodiments, system administrator 110 may comprise over seven hundred object models 306 preloaded onto model data 232. However, purchase models 628 provides for receiving additional object models 306, either for free or for a fee, to be added to model data 232 and then used by one or more users and placed in virtual environment 300.

After setup and administration of virtual environment 300, a user may select the play button 502 from main menu 500 to launch virtual environment 300.

Figure 7:
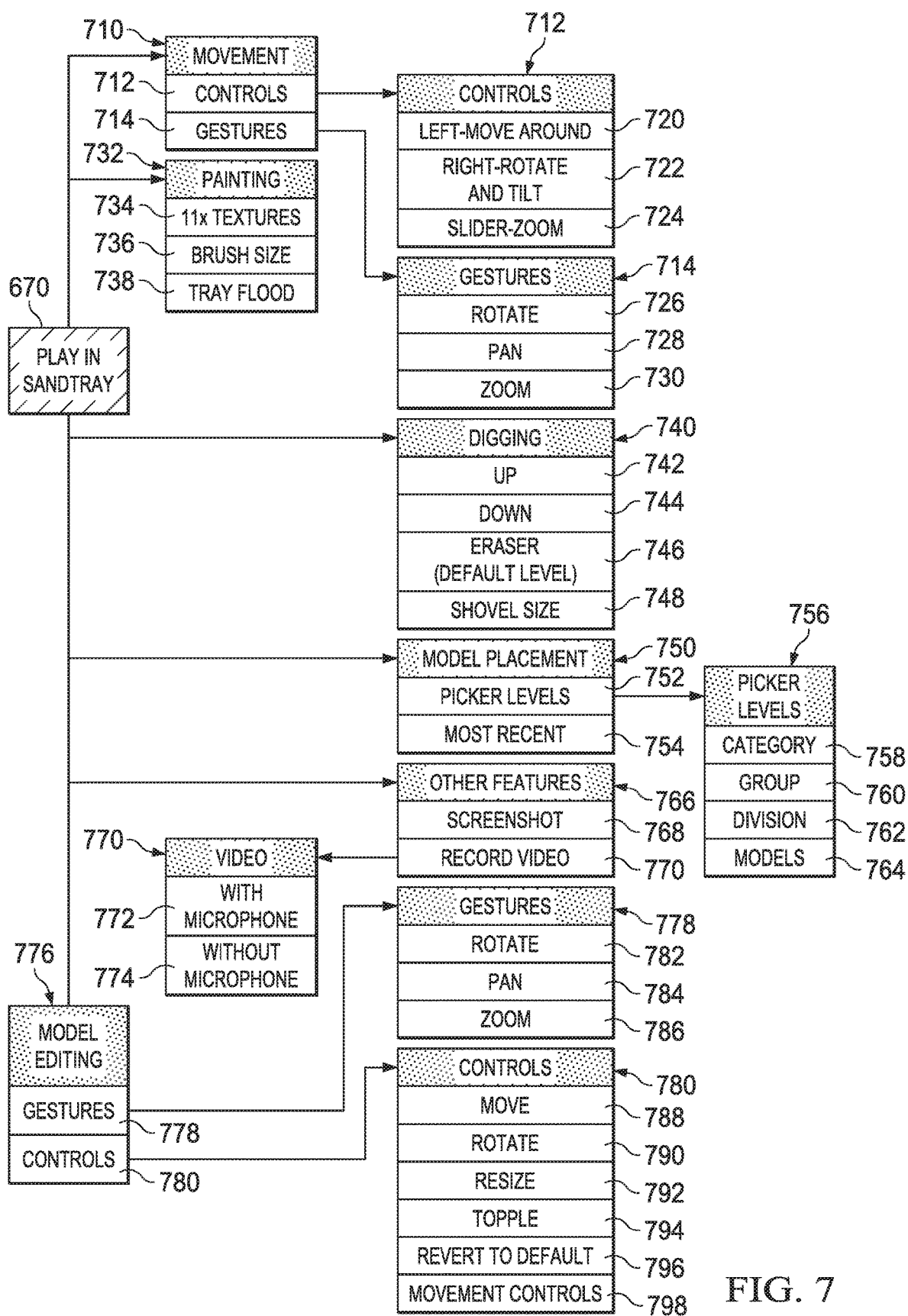
FIG. 7 illustrates an exemplary hierarchy for the various tools and options used to manipulate the virtual environment.

FIG. 7 illustrates an exemplary hierarchy 700 for the various tools and options used to manipulate virtual environment 300. For example, after secondary device 120 or primary device 130 launches virtual environment 300 by selection of a play 502 (corresponding to 670 in hierarchy 700), interface 212 presents options to, for example, control the movement of the camera angle, move virtual models, alter topography, and other like options and tools as will now be described.

Movement 710 may comprise controls 712 and gestures 714 to navigate virtual environment 300. Controls 712 may correspond to graphical or mechanical controls that permit a user to orient the view of virtual environment 300. For example, according to an embodiment, controls 712 may comprise a left controller that moves the camera around virtual environment 300 (left—move around 720), a right controller that rotates and tilts the camera angle (right—rotate and tilt 722), and a controller, such as a slider, that controls the zoom of the camera (slider zoom 724). Gestures 714 may correspond to actions through a touchscreen or other input device that correspond to rotate 726, pan 728, and zoom 730. The description of these controls and gestures will be described in connection with FIG. 8.

Figure 8:
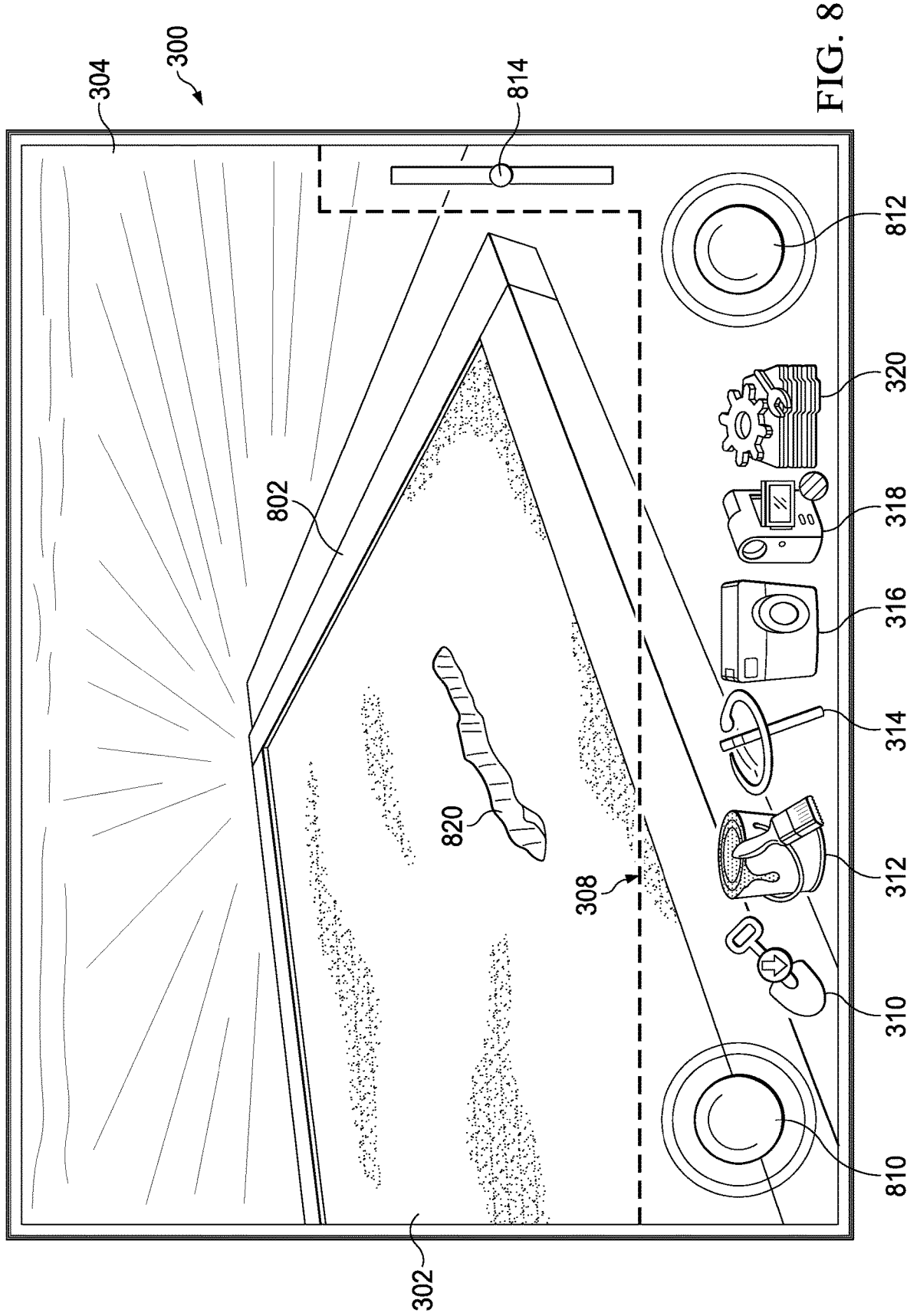
FIG. 8 illustrates an exemplary view of the virtual environment with a control interface.

FIG. 8 illustrates an exemplary view of virtual environment 300 with a control interface 308. Virtual environment 300 comprises a base layer 302, skybox 304, and border 802. Base layer 302 comprises an initial level of the topography covered in a default texture. According to an embodiment, base layer 302 represents sand and may be manipulated by digging into the sand using on one or more tools. Skybox 304 represents a background and may be changed by one or more options to represent different environments, such as a sky, outer space, a field, the interior of a building or house, or any other suitable background to reflect and modify a mood selected by a user. In addition, or as an alternative, skybox 304 may comprise a light and airy mood or a dark and gloomy mood.

Border 802 comprises an area that delineates the edges of the area of the base layer that may be manipulated and, as shown, is represented by the edges of a sandbox.

Control interface 308 comprises a menu tray that represents the various options and tools described in FIG. 7. Control interface 308 may comprise controls (left joystick 810, right joystick 812, slider 814) and tools (shovel 310, paint 312, wand 314, camera 316, video camera 318, and settings 320).

Left joystick 810 of control interface 802 corresponds to control 712 of left—move around 720 of FIG. 7. A user may manipulate left joystick 810 to change the orientation of virtual environment 300 in a first direction corresponding to moving around the virtual environment. Similarly, right joystick 812 corresponds to right—rotate and tilt 722. A user may manipulate the right joystick 812 to change the orientation of virtual environment 300 in a second direction, such as rotating and tilting virtual environment 300. Slider 814 controls zoom 724 and enlarges or shrinks virtual environment 300.

According to embodiments that comprise a touch screen or other tactile interface, gestures 714 of FIG. 7 may provide an additional or alternative input to manipulate direction and orientation of virtual environment 300. For example, virtual environment 300 may be rotated by a rotate gesture 726 that comprises, for example, making a rotation gesture with a user's fingers on the touchscreen interface. Other touchscreen gestures may control pan 728 and zoom 730, according to particular needs.

Shovel tool 310 controls digging 740. Digging 740 provides for removing or adding layers to the topography of base layer 302. Digging options may include building the topography up 742, digging the topography down 744, setting the topography back to the base level 746, and selecting the size of the shovel 748 (see FIG. 7), corresponding to the area of the base layer to be removed or the number of levels to add or dig.

For example, upon user selection of the shovel tool 310, any place the user selects on the base layer will remove or add levels to the initial level of the base layer. A small trench 820 in FIG. 8 illustrates a small indentation made by the shovel tool digging down one layer. When shovel tool 310 is used on an already excavated layer, further layers are removed.

According to embodiments, the base layer can be manipulated by building two levels up (to create topography) and removing up to two levels down (to get to an underlying surface 902 (FIG. 9)). As the user digs down to the underlying surface 902, a fluid layer appears. For more advanced users and or those desiring more detail, embodiments permit more layers of digging or building topography, such as three, four, five, or any suitable number.

Figure 9:
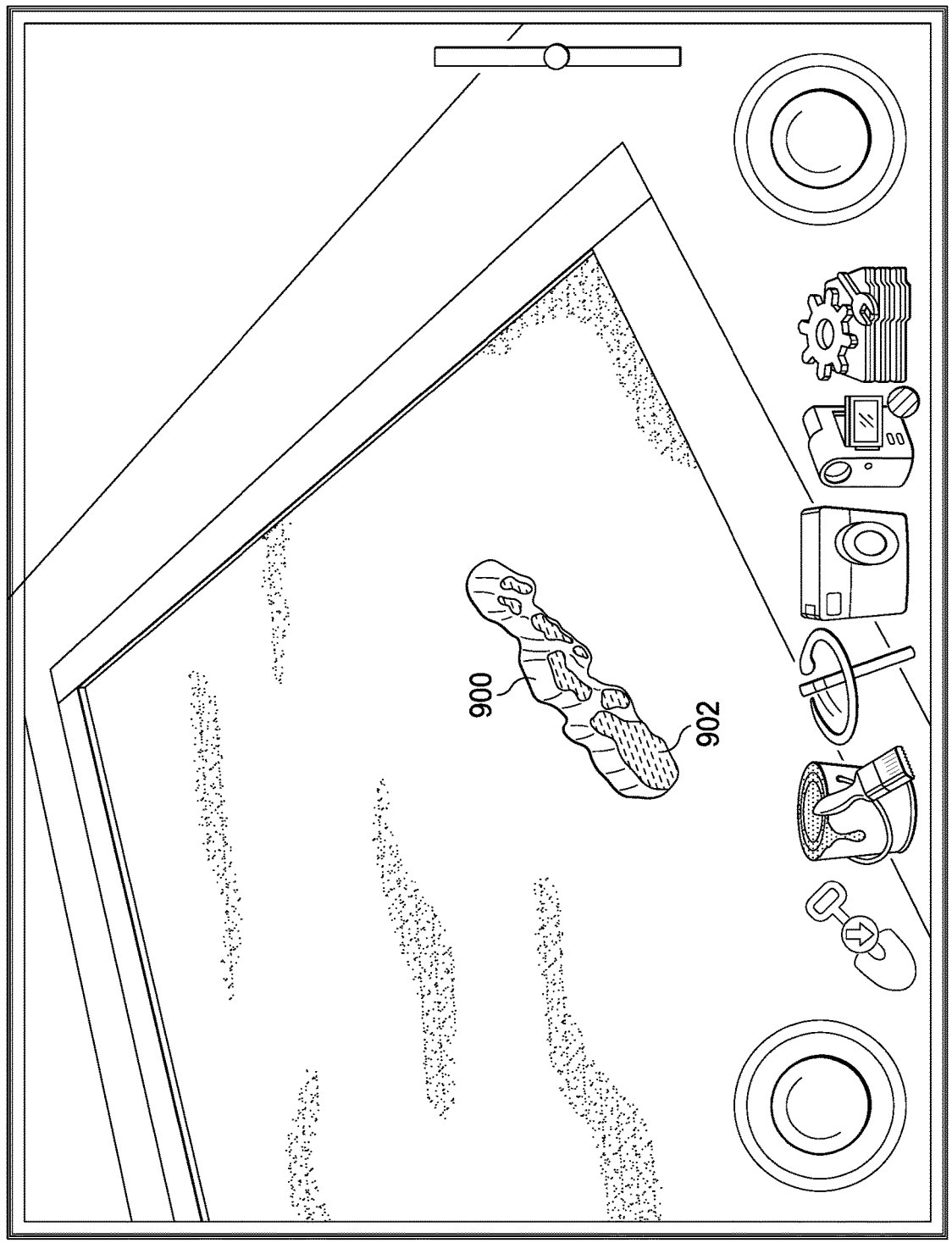
FIG. 9 illustrates an exemplary view of the virtual environment with a second layer removed.

FIG. 9 illustrates an exemplary view of virtual environment 300 with a second layer removed. As further layers are removed, an underlying surface 902 is revealed. Underlying surface 902 may comprise the bottom-most layer that cannot be excavated any further by shovel tool 310. Underlying surface 902 may comprise a water texture. In this way, a user may build an environment that is partially land and partially water depending on the levels of excavation done at various levels. The texture of underlying surface 902 may be altered according to user selection of various textures, such as changing to lava, poison, or other surfaces.

Returning to FIG. 8, a tool comprising paint brush 312 provides for the changing of one or more textures or surfaces. Selection of paint brush 312 allows for painting 732 by altering texture 734, changing brush size 736, and or covering the entire tray with one texture (tray flood 738) of FIG. 7.

Figure 10:
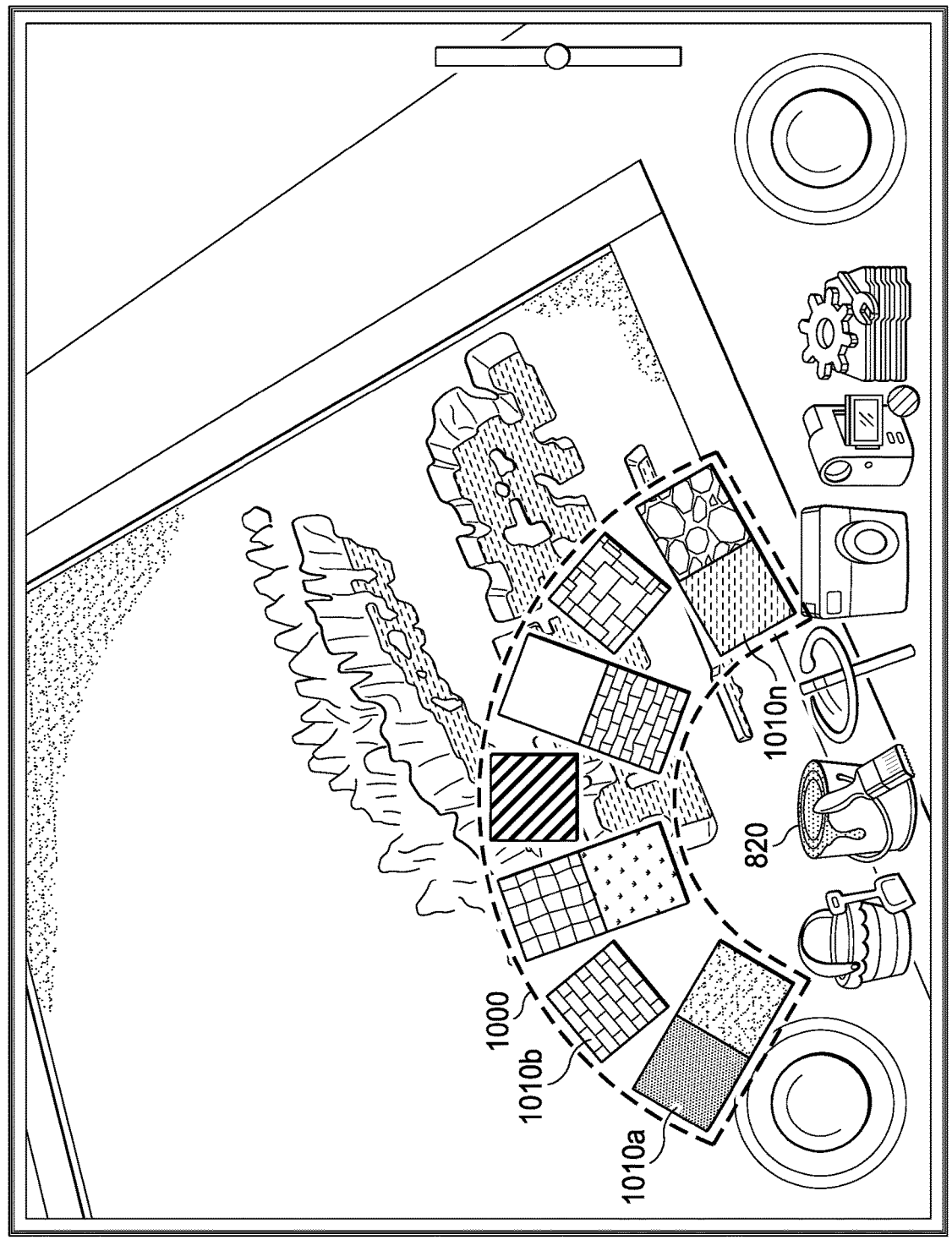
FIG. 10 illustrates features of a paint brush in accordance with an embodiment.

FIG. 10 illustrates features of paint brush 312 in accordance with an embodiment. For example, selecting paint brush 312 may generate a wheel menu 1000 that comprises one or more texture selection boxes 1010a-1010n that permit a user to click on an appropriate one or the texture selection boxes 1010a-1010n to choose a texture to change the texture of base layer 302. Once a user selects a particular texture, touching or moving a cursor over an area of base layer 302 changes the texture to the selected texture. For example, base layer 302 initially may initially comprise a texture that looks like sand. However, a user may select a brick texture 1010b, and the user may paint the brick texture over the sand texture of base layer 302 to change the appearance of the sand to look like brick. Although particular textures are shown and described, any suitable texture may be chosen according to particular needs. Such textures may include, for example, a black texture, brick, grass, hazard stripes, stone, water, lava, and the like.

Figure 11:
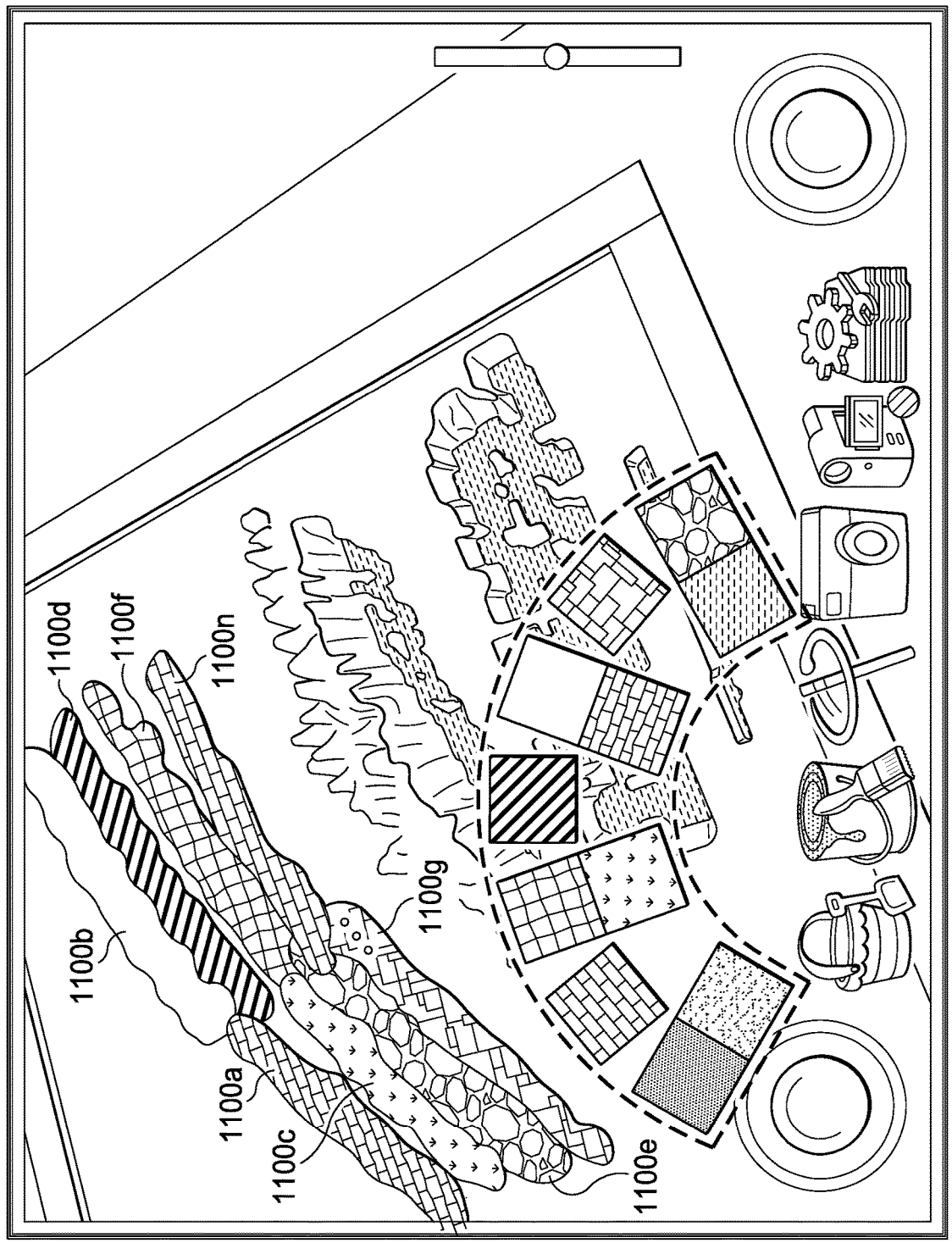
FIG. 11 illustrates a plurality of painted textures applied to a base layer of the virtual environment.

FIG. 11 illustrates a plurality of painted textures 1100a-1100n applied to base layer 302 of virtual environment 300. Painted textures 1100a-1100n may be generated by selecting the appropriate texture 1010a-1010n and using paint brush 312 to paint the textures onto base layer 302. Example painted textures 1100a-1100n are illustrated.

According to some embodiments, a user may wish to cover a larger area with a texture than is permitted with the default paint 312 tool.

Figure 12:
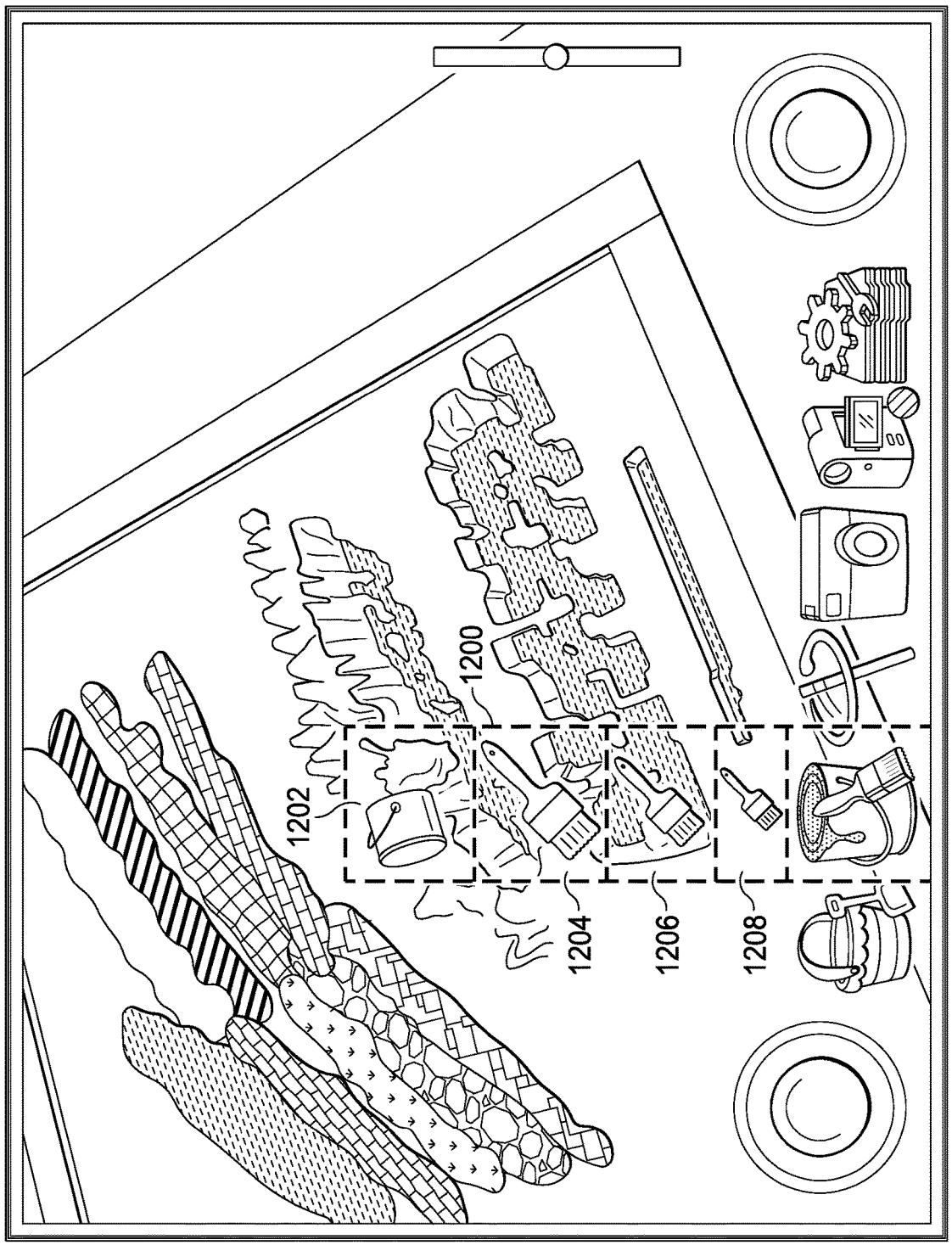
FIG. 12 illustrates a secondary paint menu according to an embodiment.

FIG. 12 illustrates a secondary paint menu 1200 according to an embodiment. According to some embodiments, if a user selects paint brush 312 by a long select, double click, or some other action, a secondary paint menu 1200 is displayed that permits the selection of brush size 736 and/or tray flood 738. A user may select tray flood 738 by choosing the icon representing a spilled paint can 1202. A user may select various brush sizes 736 by selecting an icon corresponding to a large brush 1204, medium brush 1206, or small brush 1208. Each brush provides for altering the texture of the base layer 302 in an area corresponding to the size chosen. If a user selects the tray flood 738 option, selection of anywhere on the base layer 302 will cause the texture of the entire base layer to correspond to the texture chosen.

Figure 13:
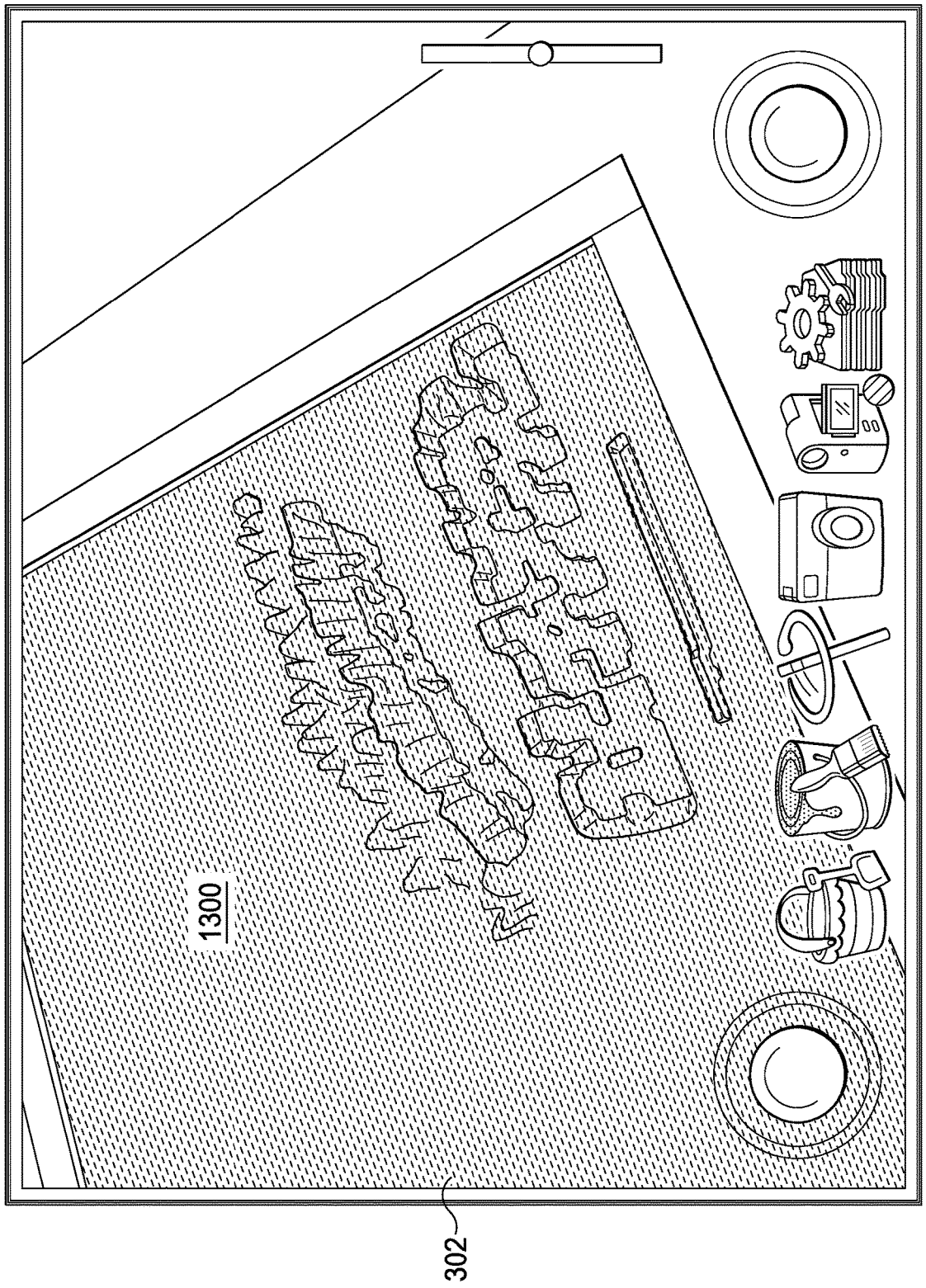
FIG. 13 illustrates applying a tray flood texture to the base layer.

FIG. 13 illustrates applying a tray flood 738 texture to the base layer. For example, after selecting the spilled paint can 1202 and a water texture from the texture wheel 1000, selecting or clicking on base layer 302 causes the entirety of the base layer 302 to comprise a water texture 1300.

In addition to altering the base layer 302 by digging or painting, virtual sand tray system 110 permits placing and manipulating object models 306 by wand 314.

Figure 14:
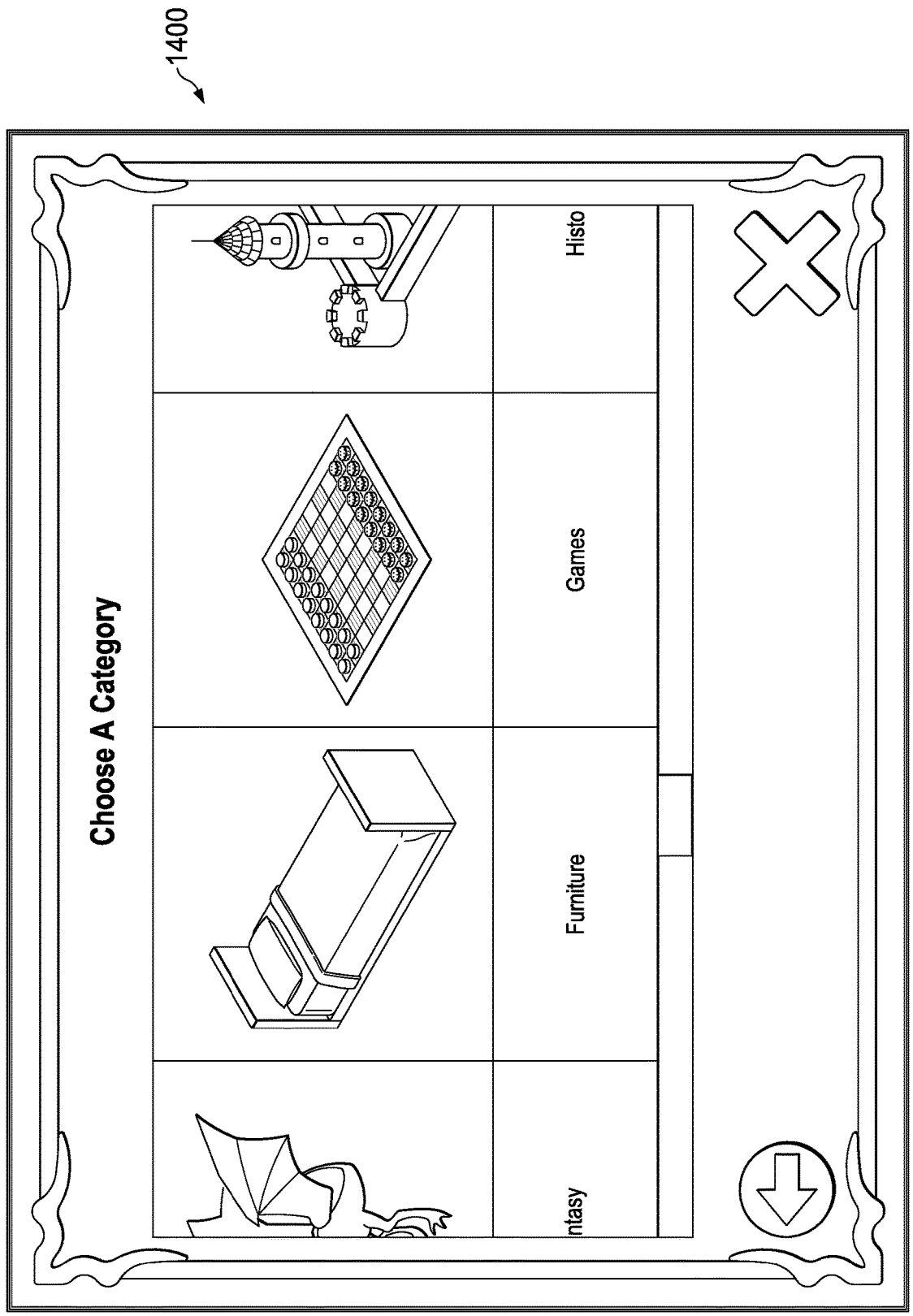
FIG. 14 illustrates an exemplary object model selection screen according to an embodiment.

FIG. 14 illustrates an exemplary object model selection screen 1400 according to an embodiment. According to embodiments, selection of wand 314 permits model placement 750 by a model selection screen 1400 (picker levels 752). The model selection screen 1400 may permit choosing between one or more object models 306 that may be organized into a hierarchy comprising one or more levels 756, categories 758, groups 760, divisions 762, and/or models 764. Object models 306 may also be chosen from a picker (most recent 754) that stores any recently used object models 306 for quicker selection.

After navigating to the appropriate object model 306 through the hierarchy (picker levels 756), a user may select the object model 306 to be placed in virtual environment 300 on the object model selection screen 1400 by selecting the appropriate model or choosing select button 1402. To view and select the most recent items, a user may select most recent items button 1404.

Figure 15:
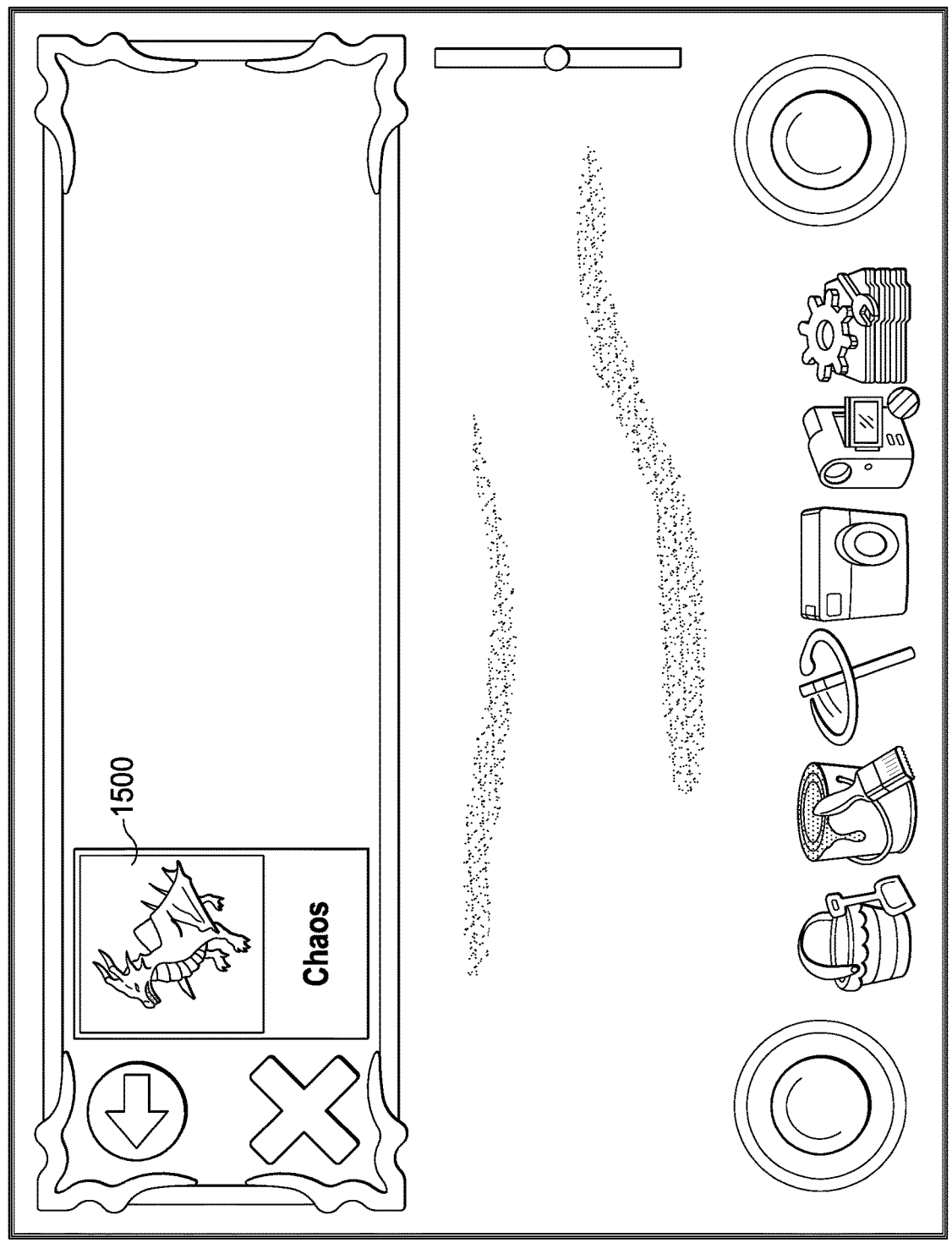
FIG. 15 illustrates a single model on the object model selection screen according to an embodiment.

FIG. 15 illustrates a single model on the object model selection screen 1400 according to an embodiment. As illustrated, a user may navigate through the hierarchy to choose a dragon object model 1500. After a user selects dragon object model 1500, interface 212 displays virtual environment 300 with a cursor to allow placement of dragon object model 1500 into virtual environment 300.

Figure 16:
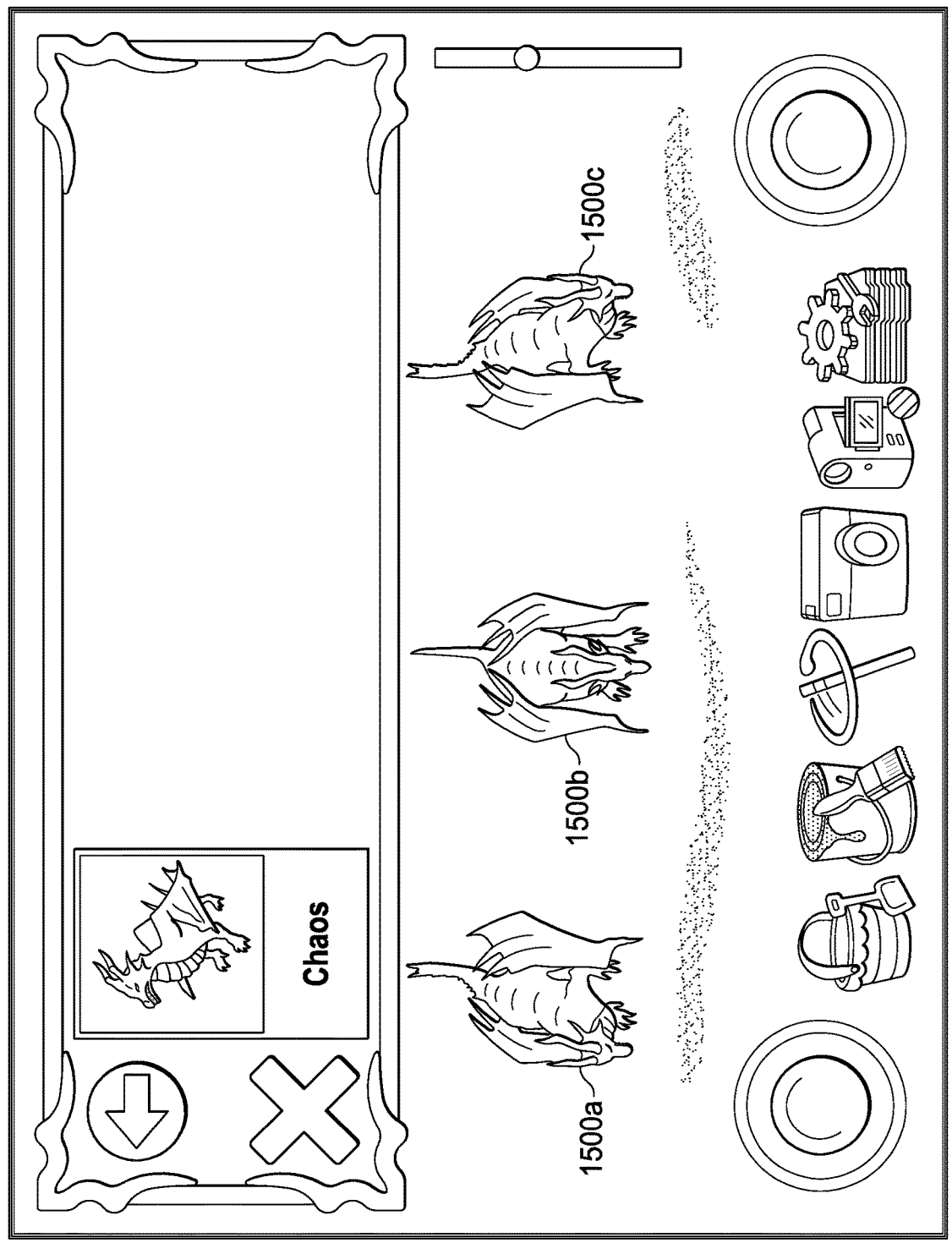
FIG. 16 illustrates object models placed in the virtual environment according to an embodiment.

FIG. 16 illustrates object models 306 placed in virtual environment 300 according to an embodiment. After a user places one or more object models 306 such as dragon object model 1500 into virtual environment 300, the user may manipulate of configure the object model 306. As illustrated, three dragon object models 1500a-1500c have been placed in virtual environment 300. According to traditional sand trays, users were limited in placing objects in the sand trays according to the number of models that the specialist was able to provide. According to embodiments, any number of object models 306 may be placed in virtual environment 300. Additionally, object models 306 may be resized to represent, for example, a family of a group of animals or characters, which was not possible in traditional sand trays.

Object models may be edited (model editing 776) by gestures 778 or controls 780. Gestures 778 may comprise rotate 782, pan 784, or zoom 786, as described above in connection with gestures 714. Here, gestures 778 manipulate the object model 306 by, for example, rotating the object model, moving the object model 306, or increasing or decreasing the size of the object model 306.

In addition, or as an alternative, if a user selects or places cursor on one or more object models, interface 212 may display one or more controls 780 for manipulating object model 306.

Figure 17:
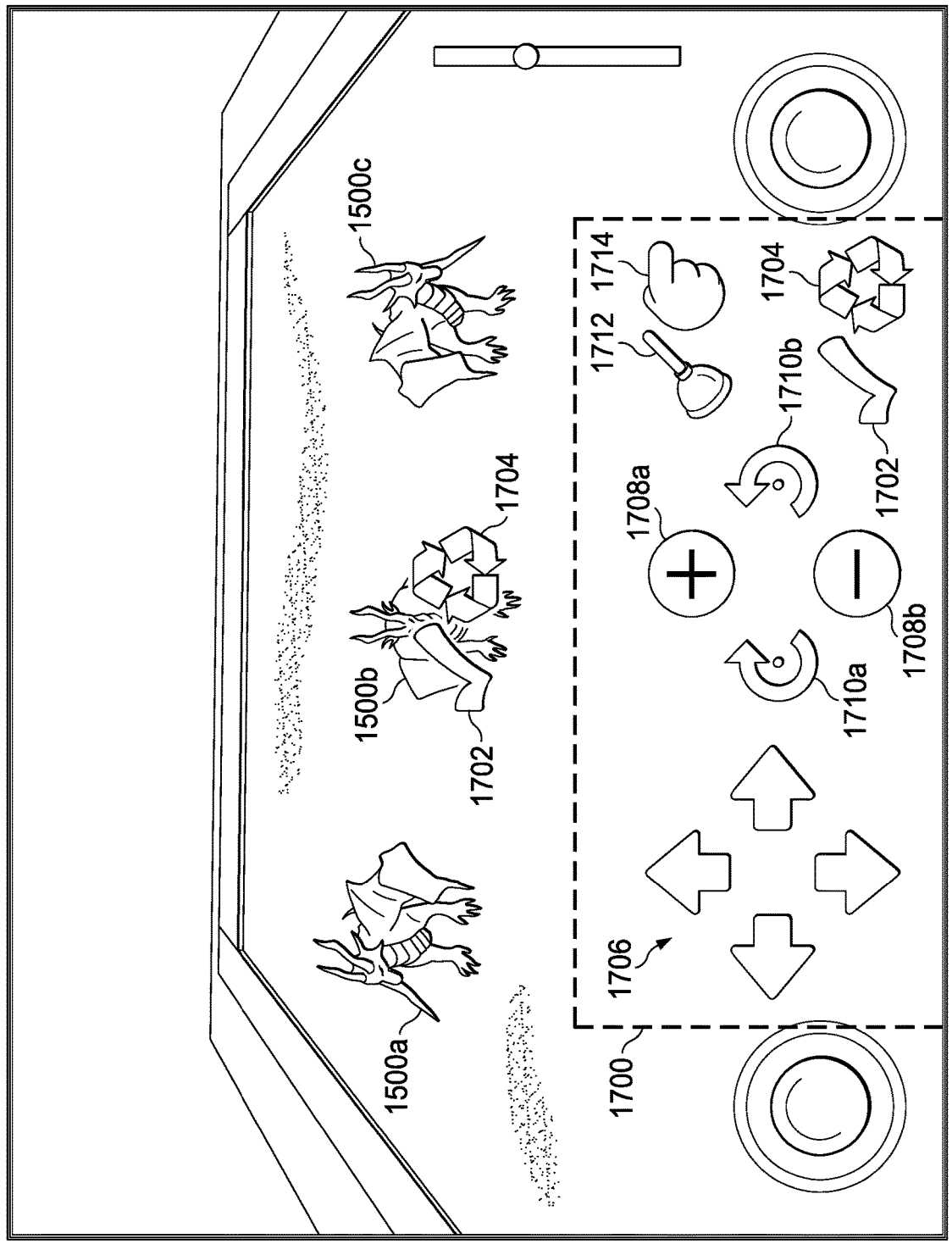
FIG. 17 illustrates exemplary controls for manipulating one or more object models according to an embodiment.

FIG. 17 illustrates exemplary controls 780 for manipulating one or more object models 306 according to an embodiment. Controls 780 may be displayed in a control interface 1700 that comprises one or more icons to manipulate object models 306. Controls 780 may comprise checkmark 1702, recycle 1704, directions 1706 (move 788), sizes 1708a-1708b (resize 792), rotate 1710a-1710b (rotate 790), plunger 1712 (revert to default 796), and pointer 1714 (topple 794).

Checkmark 1702 provides for confirming a selection or change made with controls 780. After a user makes one or more changes to object model 306, selection of checkmark 1702 confirms the changes and applies them to the object model 306 displayed in environment 300.

Recycle 1704 deletes the object model 306 by removing the object model 306 from the environment 300.

Directions 1706 allow movement of the object model 306 in relation to the base layer 302. For example, selection of an up arrow may move the object model 306 in a first direction, such as away from the camera. Selections of other arrows (down, left, right) move the object model 306 in a second, third, and fourth direction, respectively, consistent with the direction chosen.

Sizes 1708a-1708b provide for changing the size of the object model 306.

Figure 18:
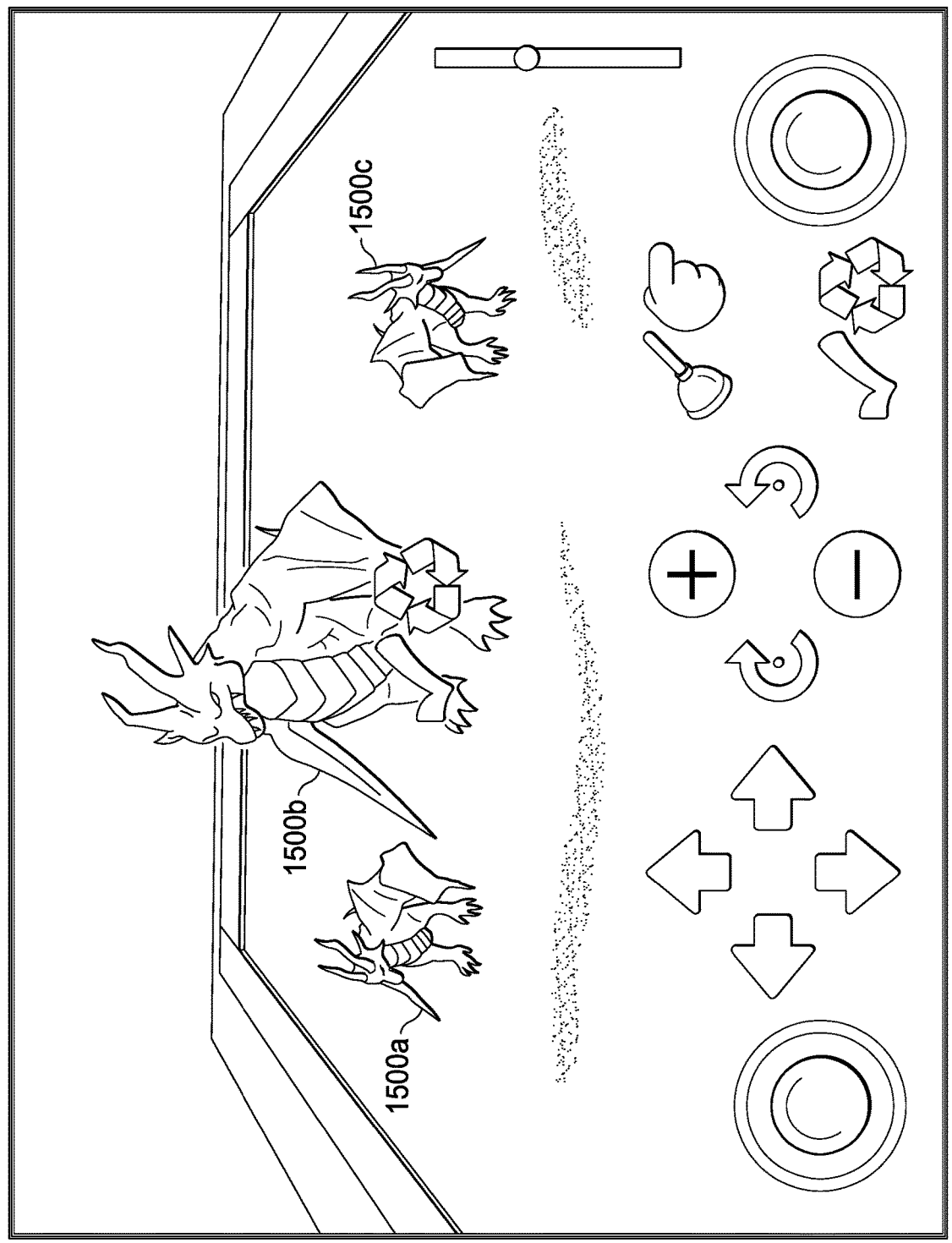
FIG. 18 illustrates the resizing of an object model according to an embodiment.

FIG. 18 illustrates the resizing of an object model 306 according to an embodiment. Here, middle dragon 1500b has been increased in size in relation to the other dragons 1500a and 1500c. The size of an object model may be increased by selecting the plus sign 1708a and decreased in size be selecting the minus sign 1708b.

Additionally, object models 306 may be rotated in relation to each other and the base layer 302. Selection of a counterclockwise rotate button 1710a rotates the object model in a counterclockwise direction. Selection of the clockwise rotate button 1710b rotates the object model in a clockwise direction.

If a user would like to discard the changes made to the object model and revert object model 306 back to a default form, the user may select plunger 1712. Plunger 1712 resets all changes made to the object model 306 and changes it back to the default size, rotation, and other manipulations. Additionally, or in the alternative, object models 306 may be removed by an explosion, or "blowing up" object models 306. Blowing up objects may be accomplished by long pressing (or other suitable selection or gesture) of the wand 314. Upon long pressing the wand 314, wand 314 changes into a bomb icon. When wand 314 appears as a bomb icon, selection of any object model 306 causes the selected object model 306 to break into smaller pieces and scatter across base layer 302, which appears as a simulated explosion of the object model 306. According to some embodiments, this explosion may be associated with a particular negative or positive connotation with the object represented by the object model 306. For example, explosion of an object model 306 that represents a person known to a client may be associated with a negative connotation with that person.

Selection of the pointer 1714 topples object model 306. Toppling of an object model 306 comprises placing object model 306 on its side or in another orientation where it is no longer in an upright position. Use of the topple feature may indicate a patient's internal state in relation to the object represented by the object model 306. When a user is finished manipulating object model 306, selection of the checkmark 1702 will save the changes made to the object model and exist the control interface 1700.

According to some embodiments, object models 306 may be further customized based on one more model-specific customizations.

Figure 19:
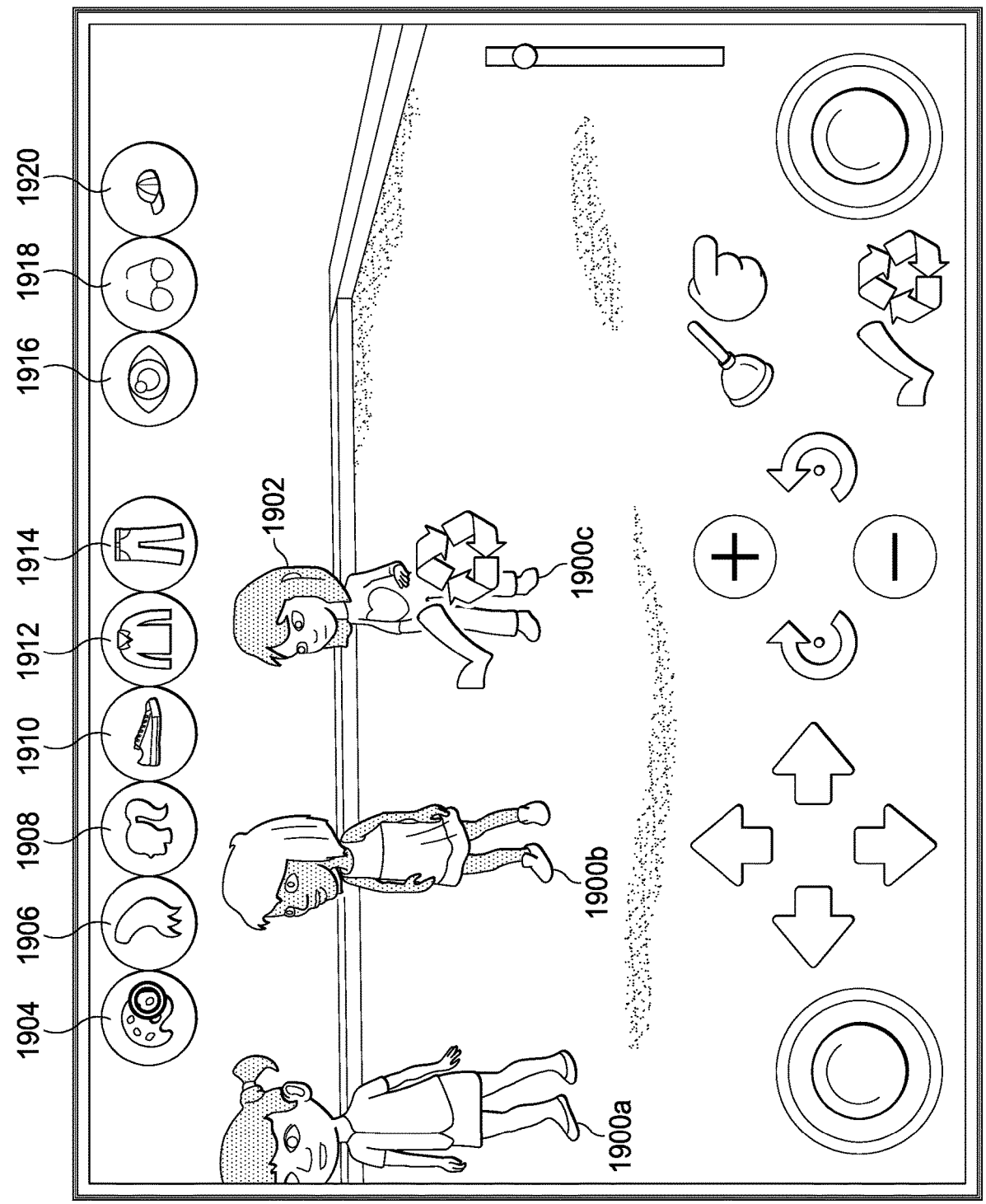
FIGS. 19 and 20 illustrate customization of human-figure object models according to an embodiment.
Figure 20:
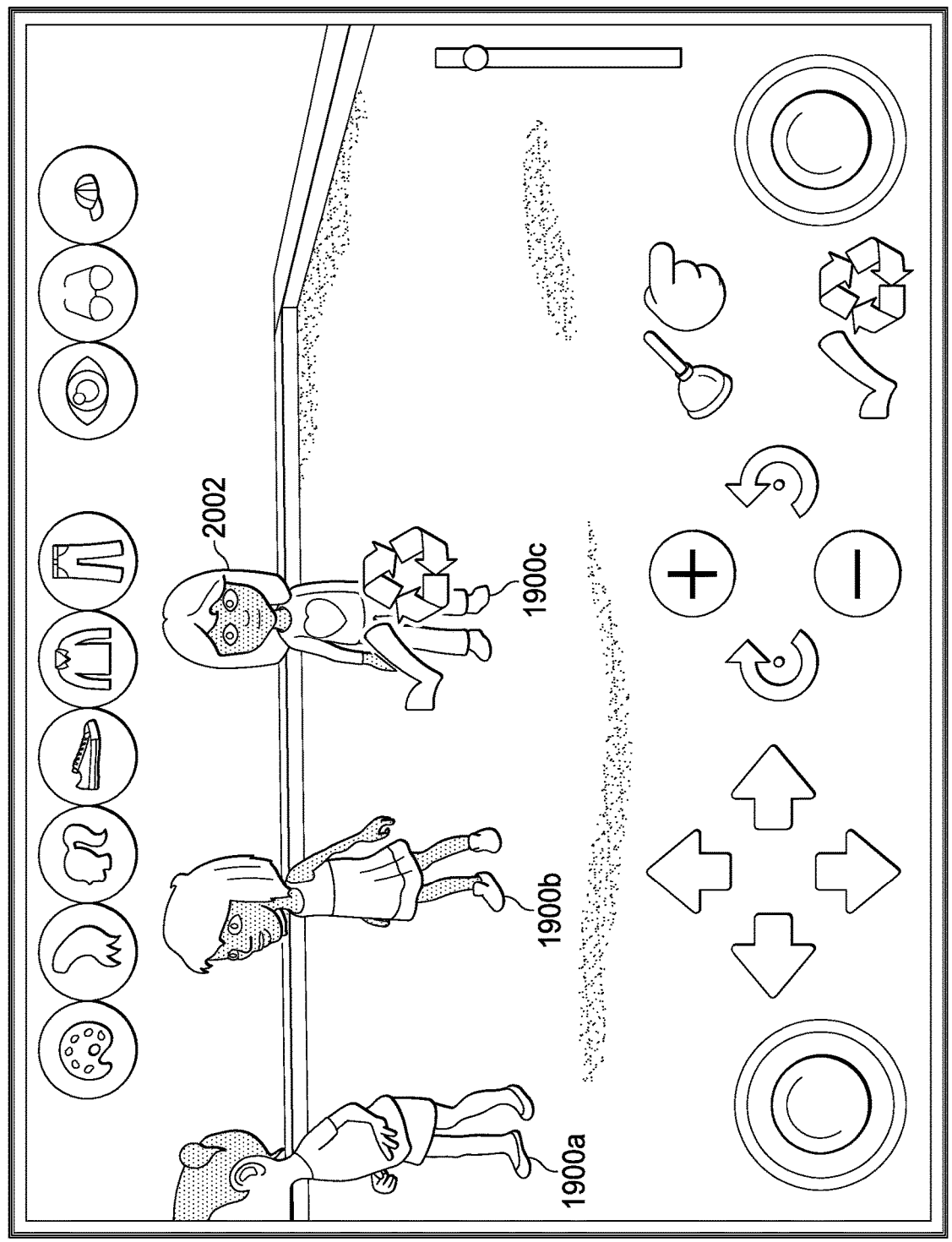

FIGS. 19 and 20 illustrate customization of human-figure object models 306 according to an embodiment. FIG. 19 illustrates three human-figure object models 1900a-1900c represented by three girls. Each girl may be customized by different ethnicity, coloring, shirt, pants, shoes, eyes, glasses, headwear and the like. For example, third girl 1900c is represented as a light-skinned girl with dark hair. Upon selection of coloring tool 1904 and a hair-tool, the girl is changed to a different-appearing girl 2002 (FIG. 20) with a dark complexion and light hair. Other customizations may be done with customization tools for head 1908, shoes 1910, shirt 1912, pants 1914, eyes 1916, eyewear 1918, and headwear 1920. Other suitable customizations may be chosen for other object models 306 according to particular needs.

In addition, or as an alternative, each of the one or more object models 306 may be animated. Such animations may include movement for flight (such as the dragon 1500) and facial expressions, such as smiling or frowning for the human-figure object models. Other animations may be included as appropriate for the particular object model 306. Animations may be controlled with a setting to turn the animations on or off according to particular needs. According to some embodiments, the animations may comprise different modes, demeanors, feelings, emotions, or the like of each model. Upon user selection of the object model 306, the object model 306 cycles through the various animations so that a user can select an animation that matches the user's internal state.

While a user is placing object models 306 and manipulating the object models 306 and virtual environment 300, secondary device 120 may automatically record the placement and manipulations and save them as recorded data 234. Additionally, camera 316 provides for taking a screenshot (screenshot 768 of other features 766) of the tray. According to embodiments, camera 316 saves an image of virtual environment 300 (and any object models 306) as a screenshot 768 from the currently displayed camera angle. The screenshot 768 may then be shared in a similar manner to the send tray 652 options described above. Additionally, screenshot 768 may be stored or shared in any suitable manner, such as storing in a photography application on the secondary device 120 or sharing by email, text message, or the like. Additionally, the camera 316 provides for changing one or more filters of virtual environment 300. For example, a filter may comprise causing virtual environment 300 to appear as if it is snowing, raining, foggy, or other precipitations or atmospheric conditions. Filters may also comprise daytime/ nighttime, night vision, or other filters according to particular needs.

Virtual environment 300 also provides for recording a video, with or without accompanying sound. Video camera 318 provides for recording a video (record video 770) of virtual environment 300.

At any point in building a virtual environment 300, selection of camera recorder 318 causes a selection box to appear on the display that presents a choice to record a video with audio (with microphone 772) or without audio (without microphone 774). The camera recorder 318 may comprise a light on the icon that flashes green when the video is recording. The recording may be stopped when the video camera 318 is selected a second time. The light on the icon may change from flashing green to solid red to indicate that the recording is stopped. When the camera recorder 318 stops recording a video, the video file may be saved locally on the secondary device 120, or remotely on primary device 130, system administrator 110, or cloud datastore 140. Video files may be stored or shared with other users in a similar manner to that described in connection with sharing trays and screenshots, as discussed above.

Settings 320 of control interface 308 provides for changing settings of virtual environment 300.

Figure 21:
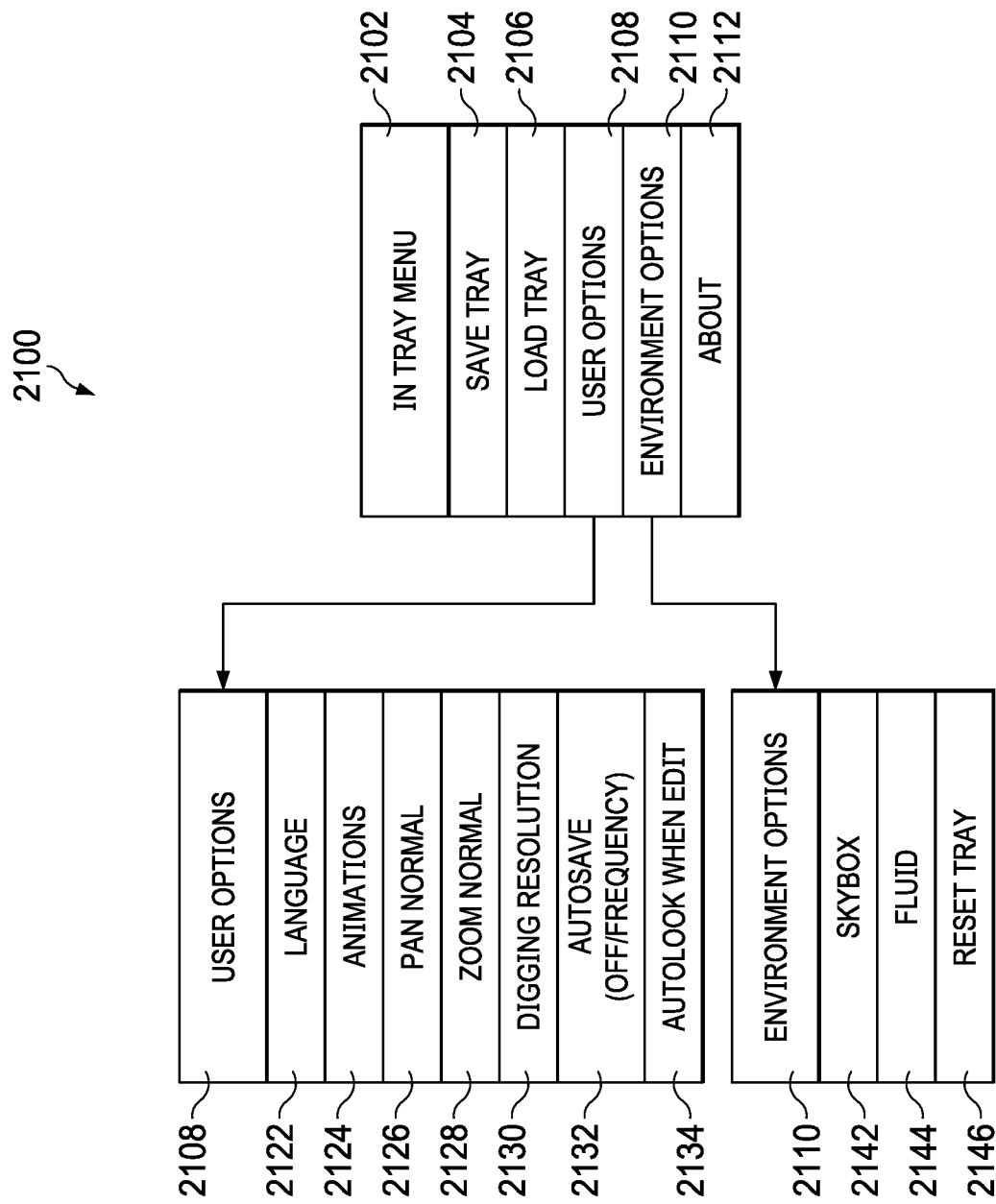
FIG. 21 illustrates an in tray menu hierarchy of the settings tool of the control interface.

FIG. 21 illustrates an in tray menu hierarchy 2100 of settings 320 tool of control interface 308. According to embodiments, in tray menu 2100 comprises save tray 2104, load tray 2106, user options 2108, environment options 2110, and about 2112.

Save tray 2104 provides for saving virtual environment 300 including the location and manipulations of any object models 306. Unlike traditional sand trays where the models or sand tray is put away after a therapy session, save tray 2104 provides for saving a sand tray digitally and reopening the sand tray right where the user left off. In this way, a user may build a larger and more comprehensive sand tray environment and provide for better understanding of the internal state of a patient. According to some embodiments, save tray 2014 comprises an automatic save (autosave) that saves the state of the tray at various time intervals, such as every one-minute, every two-minutes, or any other suitable interval of time in seconds, minutes, hours, or the like.

Load tray 2106 provides for loading virtual environments 300 including the location and manipulations of any object models 306. According to some embodiments, a tray loaded by load tray 2106 comprises a previously saved tray by a user so that the user may continue working on a previously-saved tray.

User options 2108 comprises one or more options to alter the display and features of virtual environment 300. User options 2108 may comprise language 2112, animations 21124, pan normal 2126, zoom normal 2128, digging resolution 2130, autosave 2132, and autolook 2134.

Language 2122 of user options 2108 provides for changing the language of menu options and other text of virtual environment 300 among different languages. Animations 2124 of user options 2108 provides for turning the animations of the object models 306 on or off, as described above. Pan normal 2126 and zoom normal 2128 of user options 2108 provides a zooming option for enlarging or shrinking virtual environment 300 based on gestures. Digging resolution 2130 provides an option for changing the number of layers of the base layer 302 that may be built up in topography or dug down to the underlying surface 902. As indicated above, digging resolution 2130 may comprise an option to select one, two, three, none, or any number of layers upward or downward from the base layer 302.

Autosave 2132 comprises an option to turn the autosave feature on or off and, additionally, set the time interval between autosaves. Autolook 3134 comprises an option to cause the camera angle of virtual environment 300 to automatically focus on an object model 306 when that object model 306 is selected for editing. Returning to in-tray menu 2102, selection of environment options 2110 provides for options for skybox 2142, fluid 2144, and reset tray 2146. Options for skybox 2142 provide for selecting one or more different appearances of the skybox 304. A dropdown box may provide for selecting a different skybox 304 from a selection of menu choices, as described above.

Options for fluid 2144 provide for selection of an appearance of the underlying surface 902. A dropdown box may provide for selecting a different appearance of the underlying surface 902 from a selection of menu choices, as described above. Reset tray 2146 provides for undoing all changes made to a virtual environment 300 and returning all settings and manipulations to a default state. Selection of about 2112 provides for the display of information about virtual environment 300 such as version information, license information, user information, and the like.

Reference in the foregoing specification to "one embodiment", "an embodiment", or "another embodiment" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments have been shown and described, it will be understood that various changes and modifications to the foregoing embodiments may become apparent to those skilled in the art without departing from the spirit and scope of the present invention.

What is claimed is:

1. A computer-implemented method for studying an internal state of a patient, comprising:

generating a virtual environment comprising a background skybox and a texture-mapped wireframe base layer that graphically represents a sand tray comprising a base layer;

providing one or more texture-mapped wireframe object models to be placed in the virtual environment, wherein or more object models in a first group are associated with a positive-orientation, one or more object models in a second group are associated with a negative-orientation, one or more object models in a third group are associated with one or more emotional states;

providing one or more tools to manipulate the virtual environment and the one or more object models by altering animations, behaviors, and interactions between one or more object models and the virtual environment, wherein at least some manipulations of the virtual environment are classified as constructive behaviors and at least some manipulations of the virtual environment are classified as destructive behaviors;

recording, in a computer database, an order of the placement of one or more selected object models in the virtual environment, an amount of time associated with selecting a particular object model of the one or more selected object models, and an association of the one or more selected object models, wherein the association comprises one or more of the positive-orientation, the negative-orientation, and the one or more emotional states;

recording, in the computer database, the classification of the manipulations of the virtual environment;

analyzing, with an analyzer coupled with the computer database, the recorded association of the one or more object models and the recorded classification of the manipulation of the virtual environment;

automatically correlating, by use of analyzer-performed pattern recognition of the recorded order of the placement of one or more selected object models and the recorded classification of the manipulations of the virtual environment, an internal state of a patient to with the recorded association of the one or more selected object models and the recorded classification of the manipulation of the virtual environment; and generating, with the analyzer, an analysis comprising a summary of the one or more selected object models and the correlated internal state of the patient.

2. The method of claim 1, wherein at least one of the one or more tools comprises a shovel and the shovel manipulates the base layer by adding layers to and removing layers from the base layer and wherein removing a predetermined number of layers from the base layer reveals an underlying surface.

3. The method of claim 2, wherein the virtual environment background skybox further comprises one or more user-selectable options for the skybox, and one or more user-selectable options for the underlying surface, wherein correlating an internal state of a patient is based, at least in part, on a selection from the one or more user-selectable options for the underlying surface and a selection from the one or more user-selectable options for the skybox.

4. The method of claim 3, further comprising:
customizing one or more object models at least partially based on one or more model-specific customizations;
when one or more object models are human figure-object models, customizing the one or more human figure-object models by selecting one or more facial expressions, the selected facial expression of the human figure-object models being associated with an emotion;
recording, in the computer database, the emotion associated with the selected facial expressions; and
generating, with the analyzer, an analysis of the patient, wherein the analysis comprises a summary of the recorded emotions associated with the selected facial expressions.

5. The method of claim 4, further comprising:
removing one or more human-figure object models using an explosion visualization; and
when the one or more human-figure object models removed by the explosion visualization represent one or more persons who are known to the patient, recording in the computer database a negative connotation between the patient and the one or more persons.

6. The method of claim 5, further comprising:
identifying one or more fears or emotional triggering events of a patient; and
manipulating the virtual environment and the one or more object models to cause a user to confront particular fears or deal with a particular emotional triggering event.

7. A non-transitory computer-readable medium with computer executable instruction for studying an internal state of a patient that when executed by a computer is configured to:
generate a virtual environment comprising a background skybox and a texture-mapped wireframe base layer that graphically represents a sand tray comprising a base layer;
provide one or more texture-mapped wireframe object models to be placed in the virtual environment, wherein or more object models in a first group are associated with a positive-orientation, one or more object models in a second group are associated with a negative-orientation, one or more object models in a third group are associated with one or more emotional states;
provide one or more tools to manipulate the virtual environment and the one or more object models by altering animations, behaviors, and interactions between one or more object models and the virtual environment, wherein at least some manipulations of the virtual environment are classified as constructive behaviors and at least some manipulations of the virtual environment are classified as destructive behaviors;
record, in a computer database, an order of the placement of one or more selected object models in the virtual environment, an amount of time associated with selecting a particular object model of the one or more selected object models, and an association of the one or more selected object models, wherein the association comprises one or more of the positive-orientation, the negative-orientation, and the one or more emotional states;
record, in the computer database the classification of the manipulations of the virtual environment;
analyze, with an analyzer coupled with the computer database, the recorded association of the one or more object models and the recorded classification of the manipulation of the virtual environment;
automatically correlate, by use of analyzer-performed pattern recognition of the recorded order of the placement of one or more selected object models and the recorded classification of the manipulations of the virtual environment, an internal state of a patient with the recorded association of the one or more object models and the recorded classification of the manipulation of the virtual environment; and
generate, with the analyzer, an analysis comprising a summary of the one or more selected object models and the correlated internal state of the patient.

8. The non-transitory computer-readable medium with computer executable instruction of claim 7, wherein at least one of the one or more tools comprises a shovel and the shovel manipulates the base layer by adding layers to and removing layers from the base layer and wherein removing a predetermined number of layers from the base layer reveals an underlying surface.

9. The non-transitory computer-readable medium with computer executable instruction of claim 8, wherein the virtual environment background skybox further comprises one or more user-selectable options for the skybox, and one or more user-selectable options for the underlying surface, wherein correlate an internal state of a patient is based, at least in part, on a selection from the one or more user-selectable options for the underlying surface and a selection from the one or more user-selectable options for the skybox.

10. The non-transitory computer-readable medium with computer executable instruction of claim 9, the instructions when executed are further configured to:
customize one or more object models at least partially based on one or more model-specific customizations;
when one or more object models are human figure-object models, customize the one or more human figure-object models by selecting one or more facial expressions, the selected facial expression of the human figure-object models being associated with an emotion;
record, in the computer database, the emotion associated with the selected facial expressions; and
generate, with the analyzer, an analysis of the patient, wherein the analysis comprises a summary of the recorded emotions associated with the selected facial expressions.

11. The non-transitory computer-readable medium with computer executable instruction of claim 10, the instructions when executed are further configured to:
remove one or more human-figure object models using an explosion visualization; and when the one or more human-figure object models removed by the explosion visualization represent one or more persons who are known to the patient, record in the computer database a negative connotation between the patient and the one or more persons.

12. The non-transitory computer-readable medium with computer executable instruction of claim 11, the instructions when executed are further configured to:
identify one or more fears or emotional triggering events of a patient; and
manipulate the virtual environment and the one or more object models to cause a user to confront particular fears or deal with a particular emotional triggering event.

13. A system for generating a report for an internal state of a patient, comprising:
a computer comprising an analyzer coupled with a database and configured to:
generate a virtual environment comprising a background skybox and a texture-mapped wireframe base layer that graphically represents a sand tray comprising a base layer;
provide one or more texture-mapped wireframe object models to be placed in the virtual environment, wherein or more object models in a first group are associated with a positive-orientation, one or more object models in a second group are associated with a negative-orientation, one or more object models in a third group are associated with one or more emotional states;
provide one or more tools to manipulate the virtual environment and the one or more object models by altering animations, behaviors, and interactions between one or more object models and the virtual environment, wherein at least some manipulations of the virtual environment are classified as constructive behaviors and at least some manipulations of the virtual environment are classified as destructive behaviors;
record, in the database, an order of the placement of one or more selected object models in the virtual environment, an amount of time associated with selecting a particular object model of the one or more selected object models, and an association of the one or more selected object models, wherein the association comprises one or more of the positive-orientation, the negative-orientation, and the one or more emotional states;
record, in the database, the classification of the manipulations of the virtual environment;
analyze, with the analyzer, the recorded association of the one or more object models and the recorded classification of the manipulation of the virtual environment;
automatically correlate, by use of analyzer-performed pattern recognition of the recorded order of the placement of one or more selected object models and the recorded classification of the manipulations of the virtual environment, an internal state of a patient with the association of the one or more object models and the recorded classification of the manipulation of the virtual environment; and
generate, with the analyzer, an analysis comprising a summary of the one or more selected object models and the correlated internal state of the patient.

14. The system of claim 13, wherein at least one of the one or more tools comprises a shovel and the shovel manipulates the base layer by adding layers to and removing layers from the base layer and wherein removing a predetermined number of layers from the base layer reveals an underlying surface.

15. The system of claim 14, wherein the virtual environment background skybox further comprises one or more user-selectable options for the skybox, and one or more user-selectable options for the underlying surface, wherein correlate an internal state of a patient is based, at least in part, on a selection from the one or more user-selectable options for the underlying surface and a selection from the one or more user-selectable options for the skybox.

16. The system of claim 15, wherein the computer is further configured to:
customize one or more object models at least partially based on one or more model-specific customizations;
when one or more object models are human figure-object models, customize the one or more human figure-object models by selecting one or more facial expressions, the selected facial expression of the human figure-object models being associated with an emotion;
record, in the database the emotion associated with the selected facial expressions; and
generate, with the analyzer, an analysis of the patient, wherein the analysis comprises a summary of the recorded emotions associated with the selected facial expressions.

17. The system of claim 16, wherein the computer is further configured to:
remove one or more human-figure object models using an explosion visualization; and
when the one or more human-figure object models removed by the explosion visualization represent one or more persons who are known to the patient, record in the database a negative connotation between the patient and the one or more persons.

18. The system of claim 17, wherein the computer is further configured to:
identify one or more fears or emotional triggering events of a patient; and
manipulate the virtual environment and the one or more object models to cause a user to confront particular fears or deal with a particular emotional triggering event.

* * * * *